(12) United States Patent
Wang et al.

(10) Patent No.: US 9,789,183 B1
(45) Date of Patent: Oct. 17, 2017

(54) ANTI-PD-L1 ANTIBODIES

(71) Applicant: Agency for Science, Technology and Research, Connexis (SG)

(72) Inventors: Cheng-I Wang, Singapore (SG); Hsueh Ling Janice Oh, Singapore (SG); Siok Ping Yeo, Singapore (SG)

(73) Assignee: Agency for Science, Technology and Research, Connexis (SG)

( * ) Notice: Subject to any disclaimer, the term of this patent is extended or adjusted under 35 U.S.C. 154(b) by 0 days.

(21) Appl. No.: 15/623,679

(22) Filed: Jun. 15, 2017

Related U.S. Application Data

(63) Continuation of application No. PCT/SG2016/050001, filed on Jan. 4, 2016.

(30) Foreign Application Priority Data

Jan. 9, 2015 (GB) .................................. 1500319.7

(51) Int. Cl.
| | |
|---|---|
| *A61K 39/395* | (2006.01) |
| *C07K 16/28* | (2006.01) |
| *A61K 45/06* | (2006.01) |
| *C07K 14/705* | (2006.01) |
| *G01N 33/53* | (2006.01) |
| *G01N 33/574* | (2006.01) |

(52) U.S. Cl.
CPC .......... *A61K 39/3955* (2013.01); *A61K 45/06* (2013.01); *C07K 14/70532* (2013.01); *C07K 16/2827* (2013.01); *G01N 33/53* (2013.01); *G01N 33/57484* (2013.01); *C07K 2317/34* (2013.01); *C07K 2317/54* (2013.01); *C07K 2317/55* (2013.01); *C07K 2317/622* (2013.01); *C07K 2317/76* (2013.01); *C07K 2319/30* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 7,892,540 | B2 * | 2/2011 | Chen ................. | C12N 15/1138 424/130.1 |
| 8,217,149 | B2 | 7/2012 | Irving et al. | |
| 9,175,082 | B2 * | 11/2015 | Zhou ................. | C07K 16/2818 |
| 9,402,899 | B2 * | 8/2016 | Honjo ............... | A61K 31/7088 |
| 2011/0209230 | A1 | 8/2011 | Korman et al. | |
| 2013/0122014 | A1 * | 5/2013 | Korman ............. | A61K 45/06 424/143.1 |
| 2013/0323249 | A1 | 12/2013 | Zhou et al. | |
| 2014/0065035 | A1 * | 3/2014 | Son .................. | B01L 3/502707 422/502 |

FOREIGN PATENT DOCUMENTS

| | | |
|---|---|---|
| WO | WO 2006/133396 | 12/2006 |
| WO | WO 2007/005874 | 1/2007 |
| WO | WO 2010/077634 | 7/2010 |
| WO | WO 2011/066389 | 6/2011 |
| WO | WO 2013/173223 | 11/2013 |
| WO | WO 2014/055897 | 4/2014 |
| WO | WO 2016/069727 | 5/2016 |

OTHER PUBLICATIONS

International Search Report and Written Opinion issued in PCT/SG2016/050001 dated Feb. 22, 2016.
International Preliminary Report on Patentability issued in PCT/SG2016/050001 dated Dec. 5, 2016.
Brahmer et al. (Jun. 28, 2012) The New England Journal of Medicine 366(26):2455-2465, "Safety and Activity of Anti-PD-L1 Antibody in Patients with Advanced Cancer".
Herbst et al. (Nov. 27, 2014) Nature 515:563, doi:10.1038/nature14011 "Predictive correlates of response to the anti-PD-L1 antibody MPDL3280A in cancer patients".
Quezada and Peggs, (2013) British Journal of Cancer 108:1560-1565, doi: 10.1038/bjc.2013.117, "Exploiting CTLA-4, PD-1 and PD-L1 to reactivate the host immune response against cancer".

\* cited by examiner

*Primary Examiner* — Ilia Ouspenski
(74) *Attorney, Agent, or Firm* — Swanson & Bratschun, L.L.C.

(57) ABSTRACT

Anti-PD-L1 antibodies are disclosed. Also disclosed are pharmaceutical compositions comprising such antibodies, and uses and methods using the same.

20 Claims, 26 Drawing Sheets

A1 clone

QSVLTQPPSVSAAPGQRVSISCSGRSSNIASHDVFWYQQLPGTAPKIVMYETNKRPWGIPDRFSGSKSGTSATLDIA
GLQTGDEADYYCGAWDSGLTGMLFGGGTKVTVL         (SEQ ID NO:1)

LC-CDR1:    SGRSSNIASHDVF    (SEQ ID NO:9)

LC-CDR2:    ETNKRPW          (SEQ ID NO:10)

LC-CDR3:    GAWDSGLTGML      (SEQ ID NO:11)

C2 clone

SYELTQPPSVSVAPGKTTRITCGGDNIGRKSVHWYQQRPGQAPLLLVYDDGDRPSGIPDRFSGSNSGNTATLTISGT
QAMDEADYYCQAWDSTVVFGGGTRLTVL         (SEQ ID NO:2)

LC-CDR1:    GGDNIGRKSVH      (SEQ ID NO:12)

LC-CDR2:    DDGDRPS          (SEQ ID NO:13)

LC-CDR3:    QAWDSTVV         (SEQ ID NO:14)

Figure 1A

C4 clone

QSVTQPPSVSAAPGQKVTISCSGSSSNIGNNYVSWYQQLPGTAPKLLIYDNNERLSGIPDRFSGSKSGTSATLGISG
LQTGDEADYYCGTWDSSLSVVFGGGTKLTVL    (SEQ ID NO:3)

LC-CDR1:   SGSSSNIGNNYVS (SEQ ID NO:15)

LC-CDR2:   DNNERLS    (SEQ ID NO:16)

LC-CDR3:   GTWDSSLSVVV    (SEQ ID NO:17)

H12 clone and H12_GL clone

QSVLTQPPSVSGAPGQRVTISCTGSSSNIGAGYDVHWYQQLPGTAPKLLIYGNSNRPSGVPDRFSGSKSGTSASLAI
TGLQAEDEADYYCQSYDSSLSGSYVVFGGGTKLTVL    (SEQ ID NO:4)

LC-CDR1:   TGSSSNIGAGYDVH    (SEQ ID NO:18)

LC-CDR2:   GNSNRPS    (SEQ ID NO:19)

LC-CDR3:   QSYDSSLSGSYVV    (SEQ ID NO:20)

Figure 1B

A1 clone

QVQLQQSGAEVKKPGSSVKVSCKASGGTFSSYAISWVRQAPGQGLEWMGRIIPILGIANYAQKFQGRVTITADKSTS
TAYMELSSLRSEDTAVYYCARGGSYGSLYAFDIWGQGTMVTVSS        (SEQ ID NO:5)

HC-CDR1:   SYAIS                (SEQ ID NO:21)
HC-CDR2:   RIIPILGIANYAQKFQG    (SEQ ID NO:22)
HC-CDR3:   GGSYGSLYAFDI         (SEQ ID NO:23)

C2 clone

QVQLQQSGAEVKKPGSSVKVSCKASGGTFSSYAISWVRQAPGQGLEWMGRIIPILGIANYAQKFQGRVTITADKSTS
TAYMELSSLRSEDTAVYYCARGGSYGSLYAFDIWGQGTTVTVSS        (SEQ ID NO:6)

HC-CDR1:   SYAIS                (SEQ ID NO:21)
HC-CDR2:   RIIPILGIANYAQKFQG    (SEQ ID NO:22)
HC-CDR3:   GGSYGSLYAFDI         (SEQ ID NO:23)

Figure 2A

C4 clone

QVQLQQSGAEVKKPGSSVKVSCKASGGTFSSYAISWVRQAPGQGLEWMGRIIPILGIANYAQKFQGRVTITADKSTS
TAYMELSSLRSEDTAVYYCARGGYGGNSLYAFDIWGQGTMVTVSS (SEQ ID NO:7)

HC-CDR1: SYAIS (SEQ ID NO:21)

HC-CDR2: RIIPILGIANYAQKFQG (SEQ ID NO:22)

HC-CDR3: GGYGGNSLYAFDI (SEQ ID NO:24)

H12 clone

EVQLVQSGAEVKKPGASVKVSCKASGGTFSSYAISWVRQAPGQGLEWMGRIIPILGIANYAQKFQGRVTITADKSTST
AYMELSSLRSEDTAVYYCARSGHGYSYGAFDYWGQGTL (SEQ ID NO:8)

HC-CDR1: SYAIS (SEQ ID NO:21)

HC-CDR2: RIIPILGIANYAQKFQG (SEQ ID NO:22)

HC-CDR3: SGHGYSYGAFDY (SEQ ID NO:25)

Figure 2B

H12 GL clone

QVQLVQSGAEVKKPGSSVKVSCKASGGTFSSYAISWVRQAPGQGLEWMGRIIPILGIANYAQKFQGRVTITADKSTSTAYMELSSLR
SEDTAVYYCARSGHGYSYGAFDYWGQGTLVTVSS (SEQ ID NO:35)

HC-CDR1: SYAIS (SEQ ID NO:21)

HC-CDR2: RIIPILGIANYAQKFQG (SEQ ID NO:22)

HC-CDR3: SGHGYSYGAFDY (SEQ ID NO:25)

Figure 2C

| Clone | CDR 1 | CDR 2 | CDR 3 |
|---|---|---|---|
| Light Chain | | | |
| A1 | SGRSSNIASHDVF (SEQ ID NO:9) | ETNKRPW (SEQ ID NO:10) | GAWDSGLTGML (SEQ ID NO:11) |
| C2 | GGDNIGRKSVH (SEQ ID NO:12) | DDGDRPS (SEQ ID NO:13) | QAWDSTVV (SEQ ID NO:14) |
| C4 | SGSSSNIGNNYVS (SEQ ID NO:15) | DNNERLS (SEQ ID NO:16) | GTWDSSLSVVV (SEQ ID NO:17) |
| H12 and H12_GL | TGSSSNIGAGYDVH (SEQ ID NO:18) | GNSNRPS (SEQ ID NO:19) | QSYDSSLSGSYVV (SEQ ID NO:20) |
| Heavy Chain | | | |
| A1 | SYAIS (SEQ ID NO:21) | RIIPILGIANYAQKFQG (SEQ ID NO:22) | GGSYGSLYAFDI (SEQ ID NO:23) |
| C2 | SYAIS (SEQ ID NO:21) | RIIPILGIANYAQKFQG (SEQ ID NO:22) | GGSYGSLYAFDI (SEQ ID NO:23) |
| C4 | SYAIS (SEQ ID NO:21) | RIIPILGIANYAQKFQG (SEQ ID NO:22) | GGYGGNSLYAFDI (SEQ ID NO:24) |
| H12 and H12_GL | SYAIS (SEQ ID NO:21) | RIIPILGIANYAQKFQG (SEQ ID NO:22) | SGHGYSYGAFDY (SEQ ID NO:25) |
| Consensus | SYAIS (SEQ ID NO:21) | RIIPILGIANYAQKFQG (SEQ ID NO:22) | $X_1X_2X_3X_4X_5X_6SX_7X_8AFDX_9$<br>$X_1$ = no amino acid or G<br>$X_2$ = G or S<br>$X_3$ = G or Y<br>$X_4$ = S, G or H<br>$X_5$ = Y or G<br>$X_6$ = G, N or Y<br>$X_7$ = L or Y<br>$X_8$ = Y or G<br>$X_9$ = I or Y<br>(SEQ ID NO:26) |

Figure 3

Light chain variable domains

A1 clone

>A1_aa_L
QSVLTQPPSVSAAPGQRVSISCSGRSSNIASHDVFWYQQLPGTAPKIVMYETNKRPWGIPDRFSGSKS
GTSATLDIAGLQTGDEADYYCGAWDSGLTGMLFGGGTKVTVL [SEQ ID NO. 1]

>A1_ntd_L
CAGTCTGTGTTGACGCAGCCTCCCTCAGTGTCTGCGGCCCCAGGACAGAGAGTCTCCATCTCCTGCTCTGGGAGG
AGCTCCAACATTGCCAGTCATGATGTTTTCTGGTACCAGCAACTCCCAGGAACAGCCCCCAAAATCGTCATGTAT
GAAACTAATAAACGTCCCTGGGGGATTCCTGACCGATTCTCCGGCTCCAAGTCTGGCACGTCCGCCACCCTGGAC
ATCGCCGGACTCCAGACTGGGGACGAGGCCGACTATTACTGCGGAGCATGGGATAGCGGCCTGACTGGTATGCTG
TTCGGCGGAGGGACCAAGGTGACCGTCCTA [SEQ ID NO. 27]

C2 clone

>C2_aa_L
SYELTQPPSVSVAPGKTTRITCGGDNIGRKSVHWYQQRPGQAPLLLVYDDGDRPSGIPDRFSGSNSGN
TATLTISGTQAMDEADYYCQAWDSTVVFGGGTRLTVL [SEQ ID NO. 2]

>C2_ntd_L
TCCTATGAGCTGACTCAGCCACCCTCGGTGTCAGTGGCCCCAGGAAAGACGACCAGGATTACCTGTGGGGGAGAC
AACATTGGACGTAAAAGTGTCCATTGGTATCAGCAGAGGCCAGGCCAGGCCCCTCTCCTCCTCGTCTATGATGAT
GGCGACCGGCCCTCAGGGATCCCTGACCGATTCTCTGGCTCCAACTCTGGGAACACAGCCACTCTGACCATCAGC
GGGACCCAGGCTATGGATGAGGCTGACTATTACTGTCAGGCGTGGGACAGCACCGTGGTATTCGGCGGAGGGACC
AGACTGACCGTCCTG [SEQ ID NO. 28]

C4 clone

>C4_aa_L
QSVVTQPPSVSAAPGQKVTISCSGSSSNIGNNYVSWYQQLPGTAPKLLIYDNNERLSGIPDRFSGSKS
GTSATLGISGLQTGDEADYYCGTWDSSLSVVVFGGGTKLTVL [SEQ ID NO. 3]

>C4_ntd_L
CAGTCTGTCGTGACGCAGCCGCCCTCAGTGTCTGCGGCCCCAGGACAGAAGGTCACCATCTCCTGCTCTGGAAGT
AGCTCCAACATTGGGAATAATTATGTATCCTGGTACCAGCAGCTCCCAGGAACAGCCCCCAAACTCCTCATTTAT
GACAATAATGAGCGACTCTCAGGGATTCCTGACCGATTCTCTGGTTCCAAGTCTGGCACGTCAGCCACCCTGGGC
ATCAGCGGACTCCAGACTGGGGACGAGGCCGATTATTACTGCGGCACATGGGATAGTAGCCTGAGTGTCGTGGTA
TTCGGCGGAGGGACCAAGCTGACCGTCCTA [SEQ ID NO. 29]

Figure 4A

H12 clone and H12_GL clone

>H12_aa_L
QSVLTQPPSVSGAPGQRVTISCTGSSSNIGAGYDVHWYQQLPGTAPKLLIYGNSNRPSGVPDRFSGSK
SGTSASLAITGLQAEDEADYYCQSYDSSLSGSYVVFGGGTKLTVL [SEQ ID NO. 4]

>H12_ntd_L
CAGTCTGTGCTGACGCAGCCGCCCTCAGTGTCTGGGGCCCCAGGGCAGAGGGTCACCATCTCCTGCAC
TGGGAGCAGCTCCAACATCGGGGCAGGTTATGATGTACACTGGTACCAGCAGCTTCCAGGAACAGCCC
CCAAACTCCTCATCTATGGTAACAGCAATCGGCCCTCAGGGGTCCCTGACCGATTCTCTGGCTCCAAG
TCTGGCACCTCAGCCTCCCTGGCCATCACTGGGCTCCAGGCTGAGGATGAGGCTGATTATTACTGCCA
GTCCTATGACAGCAGCCTGAGTGGTTCTTATGTGGTATTCGGCGGAGGGACCAAGCTGACCGTCCTA
[SEQ ID NO. 30]

Heavy chain variable domains

A1 clone

>A1_aa_H
QVQLQQSGAEVKKPGSSVKVSCKASGGTFSSYAISWVRQAPGQGLEWMGRIIPILGIANYAQKFQGRV
TITADKSTSTAYMELSSLRSEDTAVYYCARGGSYGSLYAFDIWGQGTMVTVSS [SEQ ID NO. 5]

>A1_ntd_H
CAGGTACAGCTGCAGCAGTCAGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGAGGGGGC
AGCTATGGTTCTCTCTATGCTTTTGATATCTGGGGCCAAGGGACAATGGTCACCGTCTCAAGC [SEQ ID NO. 31]

C2 clone

>C2_aa_H
QVQLQQSGAEVKKPGSSVKVSCKASGGTFSSYAISWVRQAPGQGLEWMGRIIPILGIANYAQKFQGRV
TITADKSTSTAYMELSSLRSEDTAVYYCARGGSYGSLYAFDIWGQGTTVTVSS [SEQ ID NO. 6]

>C2_ntd_H
CAGGTACAGCTGCAGCAGTCAGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGAGGGGGC
AGCTATGGTTCTCTCTATGCTTTTGATATCTGGGGCCAAGGGACCAGGGTCACCGTCTCAAGC [SEQ ID NO. 32]

Figure 4B

C4 clone

>C4_aa_H
QVQLQQSGAEVKKPGSSVKVSCKASGGTFSSYAISWVRQAPGQGLEWMGRIIPILGIANYAQKFQGRV
TITADKSTSTAYMELSSLRSEDTAVYYCARGGYGGNSLYAFDIWGQGTMVTVSS [SEQ ID NO. 7]

>C4_ntd_H
CAGGTACAGCTGCAGCAGTCAGGGGCTGAGGTGAAGAAGCCTGGGTCCTCGGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGGGGGGGC
TACGGTGGTAACTCCTTGTATGCTTTTGATATCTGGGGCCAAGGGACAATGGTCACCGTCTCCTCA [SEQ ID NO. 33]

H12 clone

>H12_aa_H
EVQLVQSGAEVKKPGASVKVSCKASGGTFSSYAISWVRQAPGQGLEWMGRIIPILGIANYAQKFQGRV
TITADKSTSTAYMELSSLRSEDTAVYYCARSGHGYSYGAFDYWGQGTL [SEQ ID NO. 8]

>H12_ntd_H
GAAGTGCAGCTGGTGCAGTCTGGGGCTGAGGTGAAGAAGCCTGGGGCCTCAGTGAAGGTCTCCTGCAA
GGCTTCTGGAGGCACCTTCAGCAGCTATGCTATCAGCTGGGTGCGACAGGCCCCTGGACAAGGGCTTG
AGTGGATGGGAAGGATCATCCCTATCCTTGGTATAGCAAACTACGCACAGAAGTTCCAGGGCAGAGTC
ACGATTACCGCGGACAAATCCACGAGCACAGCCTACATGGAGCTGAGCAGCCTGAGATCTGAGGACAC
GGCCGTGTATTACTGTGCGAGGTCAGGGCATGGATACAGCTATGGAGCTTTTGACTACTGGGGCCAGG
GCACCCTG [SEQ ID NO. 34]

Figure 4C

H12_GL clone

>H12_GL_aa_H
QVQLVQSGAEVKKPGSSVKVSCKASGGTFSSYAISWVRQAPGQGLEWMGRIIPILGIANYAQKFQGRVTITADKS
TSTAYMELSSLRSEDTAVYYCARSGHGYSYGAFDYWGQGTLVTVSS [SEQ ID NO. 35]

>H12_GL_ntd_H
CAGGTGCAGCTGGTGCAATCTGGGGCTGAGGTGAAGAAGCCTGGGTCCTCAGTGAAGGTCTCCTGCAAGGCTTCT
GGAGGCACCTTCAGCAGCTATGCTATCAGCTGGGTGCGACAGGCCCCTGGACAAGGGCTTGAGTGGATGGGAAGG
ATCATCCCTATCCTTGGTATAGCAAACTACGCACAGAAGTTCCAGGGCAGAGTCACGATTACCGCGGACAAATCC
ACGAGCACAGCCTACATGGAGCTGAGCAGCCTGAGATCTGAGGACACGGCCGTGTATTACTGTGCGAGGTCAGGG
CATGGATACAGCTATGGAGCTTTTGACTACTGGGGCCAGGGCACCCTGGTCACCGTCTCAAGC [SEQ ID
NO. 36]

Figure 4D

ANTI-PD-L1 ANTIBODIES

RELATED APPLICATIONS

This application is a continuation of International Application Serial No. PCT/SG2016/050001, filed Jan. 4, 2016, entitled "ANTI-PD-L1 ANTIBODIES". International Application Serial No. PCT/SG2016/050001 claims priority to GB 1500319.7, filed Jan. 9, 2015.

REFERENCE TO A "SEQUENCE LISTING"

Incorporated by reference herein in its entirety is the Sequence Listing entitled "Sequence Listing.txt", created Jun. 14, 2017, size of 18 kilobytes.

FIELD OF THE INVENTION

The present invention relates to antibodies that bind to programmed death-ligand 1 (PD-L1).

BACKGROUND TO THE INVENTION

T-cell exhaustion is a state of T-cell dysfunction that arises during many chronic infections and cancer. It is defined by poor T-cell effector function, sustained expression of inhibitory receptors and a transcriptional state distinct from that of functional effector or memory T-cells. Exhaustion prevents optimal control of infection and tumors. (E John Wherry, *Nature Immunology* 12, 492-499 (2011)).

T-cell exhaustion is characterized by the stepwise and progressive loss of T-cell functions. Exhaustion is well-defined during chronic lymphocytic choriomeningitis virus infection and commonly develops under conditions of antigen-persistence, which occur following many chronic infections including hepatitis B virus, hepatitis C virus and human immunodeficiency virus infections, as well as during tumor metastasis. Exhaustion is not an uniformly disabled setting as a gradation of phenotypic and functional defects can manifest, and these cells are distinct from prototypic effector, memory and also anergic T cells. Exhausted T cells most commonly emerge during high-grade chronic infections, and the levels and duration of antigenic stimulation are critical determinants of the process. (Yi et al., *Immunology* April 2010; 129(4):474-481).

Circulating human tumor-specific CD8$^+$ T cells may be cytotoxic and produce cytokines in vivo, indicating that self- and tumor-specific human CD8$^+$ T cells can reach functional competence after potent immunotherapy such as vaccination with peptide, incomplete Freund's adjuvant (IFA), and CpG or after adoptive transfer. In contrast to peripheral blood, T-cells infiltrating tumor sites are often functionally deficient, with abnormally low cytokine production and upregulation of the inhibitory receptors PD-1, CTLA-4, and TIM-3. Functional deficiency is reversible, since T-cells isolated from melanoma tissue can restore IFN-γ production after short-term in vitro culture. However, it remains to be determined whether this functional impairment involves further molecular pathways, possibly resembling T-cell exhaustion or anergy as defined in animal models. (Baitsch et al., *J Clin Invest.* 2011; 121(6):2350-2360).

Programmed cell death 1 (PD-1), also called CD279, is a type I membrane protein encoded in humans by the PDCD1 gene. It has two ligands, PD-L1 and PD-L2. PD-L1, also called CD274 or B7 homolog 1 (B7-H1) is a 40 kDa type I transmembrane protein encoded in humans by the CD274 gene.

PD-1 is expressed on the surface of activated T cells, and PD-L1 is expressed on the surface of antigen presenting cells (APCs), such as dendritic cells and macrophages. PD-L1 is also overexpressed in several tumors, including breast, lung, bladder, head and neck, and other cancers. When PD-L1 or PD-L2 bind to PD-1, an inhibitory signal is transmitted into the T cell, which reduces cytokine production and suppresses T-cell proliferation.

The PD-1 pathway is a key immune-inhibitory mediator of T-cell exhaustion. PD-1 functions to limit the activity of already activated T cells in the periphery during the inflammatory response to infection in order to limit autoimmunity. Blockade of this pathway can lead to T-cell activation, expansion, and enhanced effector functions. As such, PD-1 negatively regulates T cell responses. PD-1 has been identified as a marker of exhausted T cells in chronic disease states, and blockade of PD-1:PD-L1 interactions has been shown to partially restore T cell function. (Sakuishi et al., *JEM* Vol. 207, Sep. 27, 2010, pp 2187-2194).

Methods and compositions for the treatment of persistent infections and cancer by inhibiting the PD-1 pathway are disclosed in WO 2006/133396. Human monoclonal antibodies to PD-L1 are described in WO 2007/005874, US2011/209230, U.S. Pat. No. 8,217,149 and WO 2014/055897.

SUMMARY OF THE INVENTION

The present invention is concerned with antibodies, or antigen binding fragments, that bind to PD-L1. Heavy and light chain polypeptides are also disclosed. The antibodies, antigen binding fragments and polypeptides may be provided in isolated and/or purified form and may be formulated into compositions suitable for use in research, therapy and diagnosis.

In some embodiments the antibody, or antigen binding fragment, or polypeptide may be effective to restore T-cell function in T-cells, e.g. CD8$^+$ T-cells, exhibiting T-cell exhaustion or T-cell anergy.

In one aspect of the present invention an antibody, or antigen binding fragment, is provided, the amino acid sequence of the antibody may comprise the amino acid sequences i) to iii), or the amino acid sequences iv) to vi), or preferably the amino acid sequences i) to vi):

i) LC-CDR1: one of SGRSSNIASHDVF (SEQ ID NO:9), GGDNIGRKSVH (SEQ ID NO:12), SGSSS-NIGNNYVS (SEQ ID NO:15), or TGSSSNIGAGY-DVH (SEQ ID NO:18);

ii) LC-CDR2: one of ETNKRPW (SEQ ID NO:10), DDGDRPS (SEQ ID NO:13), DNNERLS (SEQ ID NO:16), or GNSNRPS (SEQ ID NO:19);

iii) LC-CDR3: one of GAWDSGLTGML (SEQ ID NO:11), QAWDSTVV (SEQ ID NO:14), GTWDSSLSVVV (SEQ ID NO:17), or QSYDSSLSGSYVV (SEQ ID NO:20);

iv) HC-CDR1: SYAIS (SEQ ID NO:21);

v) HC-CDR2: RIIPILGIANYAQKFQG (SEQ ID NO:22);

vi) HC-CDR3: $X_1X_2X_3X_4X_5X_6SX_7X_8AFDX_9$ (SEQ ID NO:26);

or a variant thereof in which one or two or three amino acids in one or more of the sequences (i) to (vi) are replaced with another amino acid, where $X_1$=absent (i.e. no amino acid) or G, $X_2$=G or S, $X_3$=G or Y, $X_4$=S, G or H, $X_5$=Y or G, $X_6$=G, N or Y, $X_7$=L or Y, $X_8$=Y or G, $X_9$=I or Y.

In some embodiments HC-CDR3 is one of GGSYG-SLYAFDI (SEQ ID NO:23), GGYGGNSLYAFDI (SEQ ID NO: 24), or SGHGYSYGAFDY (SEQ ID NO:25).

In some embodiments the antibody, or antigen binding fragment, may comprise at least one light chain variable region incorporating the following CDRs:
LC-CDR1: SGRSSNIASHDVF (SEQ ID NO:9)
LC-CDR2: ETNKRPW (SEQ ID NO:10)
LC-CDR3: GAWDSGLTGML (SEQ ID NO:11)

In some embodiments the antibody, or antigen binding fragment, may comprise at least one light chain variable region incorporating the following CDRs:
LC-CDR1: GGDNIGRKSVH (SEQ ID NO:12)
LC-CDR2: DDGDRPS (SEQ ID NO:13)
LC-CDR3: QAWDSTVV (SEQ ID NO:14)

In some embodiments the antibody, or antigen binding fragment, may comprise at least one light chain variable region incorporating the following CDRs:
LC-CDR1: SGSSSNIGNNYVS (SEQ ID NO:15)
LC-CDR2: DNNERLS (SEQ ID NO:16)
LC-CDR3: GTWDSSLSVVV (SEQ ID NO:17)

In some embodiments the antibody, or antigen binding fragment, may comprise at least one light chain variable region incorporating the following CDRs:
LC-CDR1: TGSSSNIGAGYDVH (SEQ ID NO:18)
LC-CDR2: GNSNRPS (SEQ ID NO:19)
LC-CDR3: QSYDSSLSGSYVV (SEQ ID NO:20)

In some embodiments the antibody, or antigen binding fragment, may comprise at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: $X_1X_2X_3X_4X_5X_6SX_7X_8AFDX_9$ (SEQ ID NO:26)
where $X_1$=absent or G, $X_2$=G or S, $X_3$=G or Y, $X_4$=S, G or H, $X_5$=Y or G, $X_6$=G, N or Y, $X_7$=L or Y, $X_8$=Y or G, $X_9$=I or Y.

In some embodiments the antibody, or antigen binding fragment, may comprise at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: GGSYGSLYAFDI (SEQ ID NO:23)

In some embodiments the antibody, or antigen binding fragment, may comprise at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: GGYGGNSLYAFDI (SEQ ID NO:24)

In some embodiments the antibody, or antigen binding fragment, may comprise at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: SGHGYSYGAFDY (SEQ ID NO:25)

The antibody may comprise at least one light chain variable region incorporating the CDRs shown in FIG. 1A-B or 3. The antibody may comprise at least one heavy chain variable region incorporating the CDRs shown in FIG. 2A-C or 3.

The antibody may comprise at least one light chain variable region ($V_L$) comprising the amino acid sequence of one of SEQ ID NOs 1, 9, 10, 11; or 2, 12, 13, 14; or 3, 15, 16, 17; or 4, 18, 19, 20, or one of the amino acid sequences shown in FIG. 1A-B or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs SEQ ID NOs 1, 9, 10, 11; or 2, 12, 13, 14; or 3, 15, 16, 17; or 4, 18, 19, 20, or to the amino acid sequence of the $V_L$ chain amino acid sequence shown in FIGS. 1A-B.

The antibody may comprise at least one heavy chain variable region ($V_H$) comprising the amino acid sequence of one of SEQ ID NOs 5, 21, 22, 23; or 6, 21, 22, 23; or 7, 21, 22, 24; or 8, 21, 22, 25; or 35, 21, 22, 25, or one of the amino acid sequences shown in FIGS. 2A-C or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 5, 21, 22, 23; or 6, 21, 22, 23; or 7, 21, 22, 24; or 8, 21, 22, 25; or 35, 21, 22, 25, or to the amino acid sequence of the $V_H$ chain amino acid sequence shown in FIGS. 2A-C.

The antibody may comprise at least one light chain variable region comprising the amino acid sequence of one of SEQ ID NOs 1, 9, 10, 11; or 2, 12, 13, 14; or 3, 15, 16, 17; or 4, 18, 19, 20, or one of the amino acid sequences shown in FIGS. 1A-B (or an amino acid sequence having at least 70%, more preferably one of at least 75%, 80%, 85%, 90%, 95%, 96%, 97%, 98%, 99% or 100%, sequence identity to one of SEQ ID NOs 1, 9, 10, 11; or 2, 12, 13, 14; or 3, 15, 16, 17; or 4, 18, 19, 20, or to one of the amino acid sequences of the $V_L$ chain amino acid sequence shown in FIGS. 1A-B) and at least one heavy chain variable region comprising the amino acid sequence of one of SEQ ID NOs 5, 21, 22, 23; or 6, 21, 22, 23; or 7, 21, 22, 24; or 8, 21, 22, 25; or 35, 21, 22, 25, or one of the amino acid sequence shown in FIGS. 2A-C (or an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs 5, 21, 22, 23; or 6, 21, 22, 23; or 7, 21, 22, 24; or 8, 21, 22, 25; or 35, 21, 22, 25, or to one of the amino acid sequences of the $V_H$ chain amino acid sequence shown in FIG. 2A-C).

The antibody may optionally bind PD-L1, optionally human or murine PD-L1. The antibody may optionally have amino acid sequence components as described above. The antibody may be an IgG. In one embodiment an in vitro complex, optionally isolated, comprising an antibody, or antigen binding fragment, as described herein, bound to PD-L1 is provided.

The antibody may optionally inhibit or prevent interaction or functional association between human PD-1 and human PD-L1, or between murine PD-1 and murine PD-L1. Such inhibition or prevention of interaction or functional association between PD-1 and PD-L1 may inhibit or prevent PD-L1-mediated activation of PD-1 or PD-L1/PD-1 signalling.

In one aspect of the present invention an isolated heavy chain variable region polypeptide is provided, the heavy chain variable region polypeptide comprising the following CDRs:
HC-CDR1: SYAIS (SEQ ID NO:21)
HC-CDR2: RIIPILGIANYAQKFQG (SEQ ID NO:22)
HC-CDR3: $X_1X_2X_3X_4X_5X_6SX_7X_8AFDX_9$ (SEQ ID NO:26)
where $X_1$=absent or G, $X_2$=G or S, $X_3$=G or Y, $X_4$=S, G or H, $X_5$=Y or G, $X_6$=G, N or Y, $X_7$=L or Y, $X_8$=Y or G, $X_9$=I or Y.

In some embodiments HC-CDR3 is one of GGSYG-SLYAFDI (SEQ ID NO:23), GGYGGNSLYAFDI (SEQ ID NO:24) or SGHGYSYGAFDY (SEQ ID NO:25).

In one aspect of the present invention an antibody, or antigen binding fragment, is provided, the antibody, or antigen binding fragment, comprising a heavy chain and a light chain variable region sequence, wherein:

the heavy chain comprises a HC-CDR1, HC-CDR2, HC-CDR3, having at least 85% overall sequence identity to HC-CDR1: SYAIS (SEQ ID NO:21), HC-CDR2 RIIPILGIANYAQKFQG (SEQ ID NO:22), HC-CDR3: one of $X_1X_2X_3X_4X_5X_6SX_7X_8AFDX_9$ (SEQ ID NO:26) or GGSYGSLYAFDI (SEQ ID NO:23) or GGYGNSLYAFDI (SEQ ID NO:24) or SGHGYSYGAFDY (SEQ ID NO:25), respectively, where $X_1$=absent or G, $X_2$=G or S, $X_3$=G or Y, $X_4$=S, G or H, $X_5$=Y or G, $X_6$=G, N or Y, $X_7$=L or Y, $X_8$=Y or G, $X_9$=I or Y, and the light chain comprises a LC-CDR1, LC-CDR2, LC-CDR3, having at least 85% overall sequence identity to LC-CDR1: one of SGRSSNIASHDVF (SEQ ID NO:9), GGDNIGRKSVH (SEQ ID NO:12), SGSSSNIGNNYVS (SEQ ID NO:15), or TGSSSNIGAGYDVH (SEQ ID NO:18), LC-CDR2: one of ETNKRPW (SEQ ID NO:10), DDGDRPS (SEQ ID NO:13), DNNERLS (SEQ ID NO:16), or GNSNRPS (SEQ ID NO:19), LC-CDR3: one of GAWDSGLTGML (SEQ ID NO:11), QAWDSTVV (SEQ ID NO:14), GTWDSSLSVVV (SEQ ID NO:17), or QSYDSSLSGSYVV (SEQ ID NO:20).

In some embodiments the degree of sequence identity may be one of 86%, 87%, 88%, 89%, 90%, 91%, 92%, 93%, 94%, 95%, 96%, 97%, 98%, 99%, or 100%.

In another aspect of the present invention an antibody, or antigen binding fragment, optionally isolated, is provided comprising a heavy chain and a light chain variable region sequence, wherein:

the heavy chain sequence has at least 85% sequence identity to the heavy chain sequence of SEQ ID NO:5, 6, 7, 8 or 35 (FIGS. 2A-C), and the light chain sequence has at least 85% sequence identity to the light chain sequence: SEQ ID NO:1, 2, 3 or 4 (FIGS. 1A-B). In some embodiments the degree of sequence identity may be one of 86%, 87%, 88%, 89%, 90%, 91%, 92%, 93%, 94%, 95%, 96%, 97%, 98%, 99%, or 100%.

In some embodiments the antibody, antigen binding fragment, or polypeptide further comprises variable region heavy chain framework sequences between the CDRs according to the arrangement HCFR1:HC-CDR1:HCFR2:HC-CDR2:HCFR3:HC-CDR3:HCFR4. The framework sequences may be derived from human consensus framework sequences.

In one aspect of the present invention an isolated heavy chain variable region polypeptide, optionally in combination with a light chain variable region polypeptide as described herein, is provided, the heavy chain variable region polypeptide comprising the following CDRs:

HC-CDR1: SYAIS (SEQ ID NO:21)
HC-CDR2: RIIPILGIANYAQKFQG (SEQ ID NO:22)
HC-CDR3: $X_1X_2X_3X_4X_5X_6SX_7X_8AFDX_9$ (SEQ ID NO:26) where $X_1$=absent or G, $X_2$=G or S, $X_3$=G or Y, $X_4$=S, G or H, $X_5$=Y or G, $X_6$=G, N or Y, $X_7$=L or Y, $X_8$=Y or G, $X_9$=I or Y.

In some embodiments HC-CDR3 is GGSYGSLYAFDI (SEQ ID NO:23) or GGYGGNSLYAFDI (SEQ ID NO:24) or SGHGYSYGAFDY (SEQ ID NO:25).

In some embodiments the antibody, antigen binding fragment, or polypeptide further comprises variable region light chain framework sequences between the CDRs according to the arrangement LCFR1:LC-CDR1:LCFR2:LC-CDR2:LCFR3:LC-CDR3:LCFR4. The framework sequences may be derived from human consensus framework sequences.

In some embodiments, the antibody, or antibody binding fragment, may further comprise a human constant region. For example selected from one of IgG1, IgG2, IgG3 and IgG4.

In some embodiments, the antibody, or antibody binding fragment, may further comprise a murine constant region. For example, selected from one of IgG1, IgG2A, IgG2B and IgG3.

In another aspect of the present invention, an antibody or antigen binding fragment, optionally isolated, which is capable of binding to PD-L1, which is a bispecific antibody or a bispecific antigen binding fragment is provided. The bispecific antibody or antigen binding fragment comprises (i) an antigen binding fragment or polypeptide capable of binding to PD-L1 as described herein, and (ii) an antigen binding fragment which is capable of binding to a target protein other than PD-L1.

In some embodiments, the target protein other than PD-L1 may be a cell surface receptor, e.g. a receptor expressed on the cell surface of T cells. In some embodiments the cell surface receptor may be an immune checkpoint receptor, e.g. a costimulatory receptor or an inhibitory receptor. In some embodiments, the costimulatory receptor may be selected from CD27, CD28, ICOS, CD40, CD122, OX40, 4-1 BB and GITR. In some embodiments, the inhibitory receptor may be selected from LAG-3, B7-H3, B7-H4, BTLA, CTLA-4, A2AR, VISTA, TIM-3, PD-1, and KIR.

In some embodiments, the target protein other than PD-L1 may be a cancer marker whose expression is associated with a cancer. In some embodiments, the cancer marker may be expressed at the cell surface. In some embodiments, cancer marker may be selected from HER-2, HER-3, EGFR, EpCAM, CD30, CD33, CD38, CD20, CD24, CD90, CD15, CD52, CA-125, CD34, CA-15-3, CA-19-9, CEA, CD99, CD117, CD31, CD44, CD123, CD133, ABCB5 and CD45.

In another aspect of the present invention, a composition, e.g. a pharmaceutical composition or medicament, is provided. The composition may comprise an antibody, antigen binding fragment, or polypeptide as described herein and at least one pharmaceutically-acceptable carrier, excipient, adjuvant or diluent.

In another aspect of the present invention an isolated nucleic acid encoding an antibody, antigen binding fragment, or polypeptide as described herein is provided. The nucleic acid may have a sequence of one of SEQ ID NOs 27, 28, 29, 30, 31, 32, 33, 34 or 36 (FIGS. 4A-D), or a coding sequence which is degenerate as a result of the genetic code, or may have a nucleotide sequence having at least 70% identity thereto, optionally one of 75%, 80%, 85%, 86%, 87%, 88%, 89%, 90%, 91%, 92%, 93%, 94%, 95%, 96%, 97%, 98%, 99%, or 100%.

In one aspect of the present invention there is provided a vector comprising a nucleic acid described herein. In another aspect of the present invention, there is provided a host cell comprising the vector. For example, the host cell may be eukaryotic, or mammalian, e.g. Chinese Hamster Ovary (CHO), or human or may be a prokaryotic cell, e.g. *E. coli*.

*In one aspect of the present invention a method for making an antibody, or antigen binding fragment or polypeptide as described herein is provided, the method comprising culturing a host cell as described herein under conditions suitable for the expression of a vector encoding the antibody, or antigen binding fragment or polypeptide, and recovering the antibody, or antigen binding fragment or polypeptide.*

In another aspect of the present invention an antibody, antigen binding fragment or polypeptide is provided for use in therapy, or in a method of medical treatment. In another aspect of the present invention an antibody, antigen binding fragment or polypeptide as described herein is provided for use in the treatment of a T-cell dysfunctional disorder. In another aspect of the present invention, the use of an antibody, antigen binding fragment or polypeptide as described herein in the manufacture of a medicament or pharmaceutical composition for use in the treatment of a T-cell dysfunctional disorder is provided.

In another aspect of the present invention a method of enhancing T-cell function comprising administering an antibody, antigen binding fragment or polypeptide as described herein to a dysfunctional T-cell is provided. The method may be performed in vitro or in vivo.

In another aspect of the present invention a method of treating a T-cell dysfunctional disorder is provided, the method comprising administering an antibody, antigen binding fragment or polypeptide as described herein to a patient suffering from a T-cell dysfunctional disorder.

In another aspect of the present invention an antibody, antigen binding fragment or polypeptide is provided for use in the treatment of a cancer. In another aspect of the present invention, the use of an antibody, antigen binding fragment or polypeptide as described herein in the manufacture of a medicament or pharmaceutical composition for use in the treatment of a cancer is provided.

In another aspect of the present invention a method of killing a tumour cell is provided, the method comprising administering an antibody, antigen binding fragment or polypeptide as described herein to a tumour cell. The method may be performed in vitro or in vivo. Killing of a tumour cell may, for example, be as a result of antibody dependent cell-mediated cytotoxicity (ADCC), complement dependent cytotoxicity (CDC), or through the action of a drug conjugated to the antibody, antigen binding fragment or polypeptide.

In another aspect of the present invention a method of treating a cancer is provided, the method comprising administering an antibody, antigen binding fragment or polypeptide as described herein to a patient suffering from a cancer.

The cancer may be a cancer which overexpresses PD-L1, or may comprise cells which overexpress PD-L1. The cancer may be a colorectal carcinoma or melanoma.

In another aspect of the present invention a method of modulating an immune response in a subject is provided, the method comprising administering to the subject an antibody, antigen binding fragment or polypeptide as described herein such that the immune response in the subject is modulated.

In another aspect of the present invention a method of inhibiting growth of tumor cells is provided, comprising administering an antibody, antigen binding fragment or polypeptide as described herein. The method may be in vitro or in vivo. In some embodiments a method of inhibiting growth of tumor cells in a subject is provided, the method comprising administering to the subject a therapeutically effective amount of an antibody, antigen binding fragment or polypeptide as described herein.

In another aspect of the present invention a method is provided, the method comprising contacting a sample containing, or suspected to contain, PD-L1 with an antibody or antigen binding fragment, as described herein, and detecting the formation of a complex of antibody, or antigen binding fragment, and PD-L1.

In another aspect of the present invention a method of diagnosing a disease or condition in a subject is provided, the method comprising contacting, in vitro, a sample from the subject with an antibody, or antigen binding fragment, as described herein, and detecting the formation of a complex of antibody, or antigen binding fragment, and PD-L1.

In a further aspect of the present invention the use of an antibody, or antigen binding fragment, as described herein, for the detection of PD-L1 in vitro is provided. In another aspect of the present invention the use of an antibody, or antigen binding fragment, as described herein, as an in vitro diagnostic agent is provided.

In methods of the present invention the antibody, antigen binding fragment or polypeptide may be provided as a composition as described herein.

In some embodiments the antibody may be clone A1, C2, C4, H12 or H12_GL as described herein.

DESCRIPTION

Antibodies

Antibodies according to the present invention preferably bind to PD-L1 (the antigen), preferably human or murine PD-L1, optionally with a $K_D$ in the range 0.1 to 4 nM.

Antibodies according to the present invention may be provided in isolated form.

Antibodies according to the present invention may exhibit least one of the following properties:
   a) binds to human, mouse or cynomolgus macaque PD-L1 with a $K_D$ of 1 µM or less, preferably one of ≤10 nM, ≤1 nM ≤500 pM, ≤400 pM or ≤300 pM;
   b) does not substantially bind to human PD-1, PD-L2, TIM-3, LAG3, ICOS, CTLA-4, BTLA or CD28
   c) inhibits or prevents interaction between human PD-1 and human PD-L1 or inhibits or prevents interaction between murine PD-1 and murine PD-L1;
   d) increases T-cell proliferation in an Mixed Lymphocyte Reaction (MLR) assay (e.g. see Bromelow et al *J. Immunol Methods*, 2001 Jan. 1; 247(1-2):1-8);
   e) increases interferon-gamma production in an MLR assay;
   f) increases interferon-gamma production by tumour infiltrating lymphocytes ex vivo;
   g) increases interferon-gamma production by lymphocytes in response to infection
   h) inhibits tumour growth, optionally in vivo;
   i) binds to PD-L1 (optionally human PD-L1) with greater affinity than, or with similar affinity to, affinity of binding by atezolizumab (MPDL3280A; RG7446);
   j) binds to PD-L1 (optionally human PD-L1) with greater avidity than, or with similar avidity to, avidity of binding by atezolizumab;
   k) inhibits or prevents interaction between PD-L1 and PD-1 (optionally human PD-L1 and human PD-1) to a greater extent than, or to a similar extent to, inhibition/prevention of interaction by atezolizumab.

By "antibody" we include a fragment or derivative thereof, or a synthetic antibody or synthetic antibody fragment.

In view of today's techniques in relation to monoclonal antibody technology, antibodies can be prepared to most antigens. The antigen-binding portion may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Monoclonal antibodies (mAbs) are useful in the methods of the invention and are a homogenous population of antibodies specifically targeting a single epitope on an antigen.

Polyclonal antibodies are useful in the methods of the invention. Monospecific polyclonal antibodies are preferred. Suitable polyclonal antibodies can be prepared using methods well known in the art.

Antigen binding fragments of antibodies, such as Fab and $Fab_2$ fragments may also be used/provided as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parent antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sci. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. by a flexible oligopeptide.

Fab, Fv, ScFv and dAb antibody fragments can all be expressed in and secreted from E. coli, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic antibodies which bind to PD-L1 may also be made using phage display technology as is well known in the art.

The present application also provides an antibody or antigen binding fragment which is capable of binding to PD-L1, and which is a bispecific antibody or a bispecific antigen binding fragment. In some embodiments, the bispecific antibody or bispecific antigen binding fragment may be isolated.

In some embodiments, the bispecific antibodies and bispecific antigen binding fragments comprise an antigen binding fragment or a polypeptide according to the present invention. In some embodiments, the bispecific antibodies and bispecific antigen binding fragments comprise an antigen binding fragment capable of binding to PD-L1, wherein the antigen binding fragment which is capable of binding to PD-L1 comprises or consists of an antigen binding fragment or a polypeptide according to the present invention.

In some embodiments the bispecific antibodies and bispecific antigen binding fragments comprise an antigen binding fragment capable of binding to PD-L1, and an antigen binding fragment capable of binding to another target protein.

The antigen binding fragment capable of binding to another target protein may be capable of binding to another protein other than PD-L1.

In some embodiments, the target protein may be a cell surface receptor. In some embodiments, the target protein may be a cell surface receptor expressed on the cell surface of an immune cell, e.g. T cell. In some embodiments the cell surface receptor may be an immune checkpoint receptor. In some embodiments, the immune checkpoint receptor may be a costimulatory receptor. In some embodiments, the costimulatory receptor may be selected from CD27, CD28, ICOS, CD40, CD122, OX40, 4-1 BB and GITR. In some embodiments, the immune checkpoint receptor may be an inhibitory receptor. In some embodiments, the inhibitory receptor may be selected from LAG-3, B7-H3, B7-H4, BTLA, CTLA-4, A2AR, VISTA, TIM-3, PD-1, and KIR.

In some embodiments, the target protein may be a cancer marker. That is, the target protein may be a protein whose expression (e.g. upregulated expression) is associated with a cancer. In some embodiments, the cancer marker may be expressed at the cell surface. In some embodiments the cancer marker may be a receptor. In some embodiments, the cancer marker may be selected from HER-2, HER-3, EGFR, EpCAM, CD30, CD33, CD38, CD20, CD24, CD90, CD15, CD52, CA-125, CD34, CA-15-3, CA-19-9, CEA, CD99, CD117, CD31, CD44, CD123, CD133, ABCB5 and CD45.

In some embodiments, the antigen binding fragment for CD27 may comprise the CDRs, light and heavy chain variable domains or other CD27 binding fragment of e.g. anti-CD27 antibody clone 0323 (Millipore) or varlilumab (Celldex Therapeutics). In some embodiments, the antigen binding fragment for CD28 may comprise the CDRs, light and heavy chain variable domains or other CD28 binding fragment of e.g. anti-CD28 antibody clone CD28.6 (eBioscience), clone CD28.2, clone JJ319 (Novus Biologicals), clone 204.12, clone B-23, clone 10F3 (Thermo Scientific Pierce Antibodies), clone 37407 (R&D Systems), clone 204-12 (Abnova Corporation), clone 15E8 (EMD Millipore), clone 204-12, clone YTH913.12 (AbD Serotec), clone B-T3 (Acris Antibodies), clone 9H6E2 (Sino Biological), clone C28/77 (MyBioSource.com), clone KOLT-2 (AL-PCO), clone 152-2E10 (Santa Cruz Biotechnology), or clone XPH-56 (Creative Diagnostics). In some embodiments, the antigen binding fragment for ICOS may comprise the CDRs, light and heavy chain variable domains or other ICOS binding fragment of e.g. anti-ICOS antibody clone ISA-3 (eBioscience), clone SP98 (Novus Biologicals), clone 1G1, clone 3G4 (Abnova Corporation), clone 669222 (R&D Systems), clone TQ09 (Creative Diagnostics), or clone C398.4A (BioLegend). In some embodiments, the antigen binding fragment for CD40 may comprise the CDRs, light and heavy chain variable domains or other CD40 binding fragment of e.g. anti-CD40 antibody clone 82111 (R&D Systems), or ASKP1240 (Okimura et al., AM J Transplant (2014) 14(6) 1290-1299). In some embodiments, the antigen binding fragment for CD122 may comprise the CDRs, light and heavy chain variable domains or other CD122 binding fragment of anti-CD122 antibody clone mikβ2 (PharMingen). In some embodiments, the antigen binding fragment for OX40 may comprise the CDRs, light and heavy chain variable domains or other OX40 binding fragment of e.g. anti-OX40 antibodies disclosed in US 20130280275, U.S. Pat. No. 8,283,450 or WO2013038191, e.g. clone 12H3 or clone 20E5. In some embodiments, the antigen binding fragment for 4-1 BB may comprise the CDRs, light and heavy chain variable domains or other 4-1 BB binding fragment of e.g. anti-4-1BB antibody PF-05082566 (Fisher et al., Cancer Immunol Immunother (2012) 61: 1721-1733), or urelumab (BMS-665513; Bristol-Myers Squibb; Li and Liu, Clin Pharmacol (2013); 5: 47-53). In some embodiments, the antigen binding fragment for GITR may comprise the CDRs, light and heavy chain variable domains or other GITR binding fragment of e.g. anti-GITR antibody TRX-518 (Tolerx®; Schaer et al., (2010) 11(12): 1378-1386), or clone AIT 518D (LifeSpan Biosciences). In some embodiments, the antigen binding fragment for LAG3 may comprise the CDRs, light and heavy chain variable domains or other LAG3 binding fragment of e.g. anti-LAG3 antibody clone 17B4 (Enzo Life Sciences), clone 333210 (R&D Systems), or clone 14L676 (United States Biological). In some embodiments, the antigen binding fragment for B7-H3 may comprise the CDRs, light and heavy chain variable domains or other B7-H3 binding fragment of e.g. anti-B7-H3 antibody clones disclosed in US 20130078234, WO2014160627 or WO2011109400. In some embodiments, the antigen binding fragment for B7-H4 may comprise the CDRs, light and heavy chain variable domains or other B7-H4 binding fragment of e.g. anti-B7-H4 antibody clones disclosed in WO2013067492, WO2009073533 or EP2934575, for example clone 2H9. In some embodiments, the antigen binding fragment for BTLA may comprise the CDRs, light and heavy chain variable domains or other BTLA binding fragment of e.g. anti-BTLA antibody clone 1B7, clone 2G8, clone 4C5 (Abnova Corporation), clone 4B8 (antibodies-online), clone MIH26 (Thermo Scientific Pierce Antibodies), clone UMAB61 (OriGene Technologies), clone 330104 (R&D Systems), clone 1B4 (LifeSpan BioSciences), clone 440205, clone 5E7 (Creative Diagnostics). In some embodiments, the antigen binding fragment for CTLA4 may comprise the CDRs, light and heavy chain variable domains or other CTLA4 binding fragment of e.g. anti-CTLA4 antibody clone 2F1, clone 1F4 (Abnova Corporation), clone 9H10 (EMD Millipore), clone BNU3 (GeneTex), clone 1E2, clone AS32 (LifeSpan BioSciences) clone A3.4H2.H12 (Acris Antibodies), clone 060 (Sino Biological), clone BU5G3 (Creative Diagnostics), clone MIH8 (MBL International), clone A3.6B10.G1, or clone L3D10 (BioLegend). In some embodiments, the antigen binding fragment for A2AR may comprise the CDRs, light and heavy chain variable domains or other A2AR binding fragment of e.g. anti-A2AR antibody clone 7F6 (Millipore; Koshiba et al. Molecular Pharmacology (1999); 55: 614-624. In some embodiments, the antigen binding fragment for VISTA may comprise the CDRs, light and heavy chain variable domains or other VISTA binding fragment of e.g. anti-VISTA antibodies disclosed in WO2015097536 or US20140105912, e.g. clone 13F3. In some embodiments, the antigen binding fragment for TIM-3 may comprise the CDRs, light and heavy chain variable domains or other TIM-3 binding fragment of e.g. anti-TIM-3 antibody clone F38-2E2 (BioLegend), clone 2E2 (Merck Millipore; Pires da Silva et al., Cancer Immunol Res (2014) 2(5): 410-422), clone 6B6E2, clone 024 (Sino Biological) clone 344801 (R&D Systems), clone E-18, clone H-191 (Santa Cruz Biotechnology), or clone 13A224 (United States Biological). In some embodiments, the antigen binding fragment for PD-1 may comprise the CDRs, light and heavy chain variable domains or other PD-1 binding fragment of e.g. anti-PD-1 antibody clone J116, clone MIH4 (eBioscience), clone 7A11B1 (Rockland Immunochemicals Inc.), clone 192106 (R&D Systems), clone J110, clone J105 (MBL International), clone 12A7D7, clone 7A11B1 (Abbiotec), clone #9X21 (MyBioSource.com), clone 4H4D1 (Proteintech Group), clone D3W4U, clone D3O4S (Cell Signaling Technology), clone RMP1-30, clone RMP1-14 (Merck Millipore), clone EH12.2H7 (BioLegend), clone 10B1227 (United States Biological), clone UMAB198, clone UMAB197 (Origene Technologies), nivolumab (BMS-936558), lambrolizumab, or anti-PD-1 antibodies described in WO 2010/077634 or WO 2006/121168. In some embodiments, the antigen binding fragment for KIR may comprise the CDRs, light and heavy chain variable domains or other KIR binding fragment of e.g. anti-KIR antibody clone 1-7F9 (Romagne et al., Blood (2009) 114(13): 2667-2677), lirilumab (BMS-986015; Sola et al., J Immunother Cancer (2013); 1:P40) or anti-KIR antibodies described in US 2015/0344576 or WO 2014/066532. In some embodiments, the antigen binding fragment for HER-2 may comprise the CDRs, light and heavy chain variable domains or other HER-2 binding fragment of e.g. anti-HER-2 antibody trastuzumab (Herceptin), or anti-HER-2 antibodies described in WO 2003/006509 or WO 2008/019290. In some embodiments, the antigen binding fragment for HER-3 may comprise the CDRs, light and heavy chain variable domains or other HER-3 binding fragment of e.g. anti-HER-3 antibody clone MM-121 (Lyu et al., Int. J Clin Exp Pathol (2015) 8(6): 6143-6156), MEHD7945A (Schaefer et al., Cancer Cell (2011) 20(4): 472-486), AMG 888 (U3-1287; Aurisicchio et al., Oncotarget (2012) 3(8): 744-758) or anti-HER-3 antibodies described in WO2008/100624 or WO 2013048883. In some embodiments, the antigen binding fragment for EGFR may comprise the CDRs, light and heavy chain variable domains or other EGFR binding fragment of e.g. anti-EGFR antibody panitumumab (ABX-EGF; Vectibix), cetuximab (Erbitux), nimotuzumab, matazumab (EMD 7200) or antibody clone 048-006 (Sogawa et al., Nucl Med Comm (2012) 33(7): 719-725). In some embodiments, the antigen binding fragment for EpCAM may comprise the CDRs, light and heavy chain variable domains or other EpCAM binding fragment of e.g. anti-EpCAM antibody edrecolomab, ING-1, 3622W4, or adecatumumab (Munz et al., Cancer Cell Int (2010) 10:44). In some embodiments, the antigen binding fragment for CD30 may comprise the CDRs, light and heavy chain variable domains or other CD30 binding fragment of e.g. anti-CD30 antibody brentuximab (cAC10), clone SGN-30 (Wahl et al., Cancer Res 2002 62(13):3736-3742), clone 5F11 (Borchmann et al., Blood (2003) 102(1): 3737-3742), or anti-CD30 antibodies described in WO 1993024135 or WO 2003059282. In some embodiments, the antigen binding fragment for CD33 may comprise the CDRs, light and heavy chain variable domains or other CD33 binding fragment of e.g. anti-CD33 antibody lintuzumab (SGN-33), gemtuzumab (Mylotarg), or clone hP67.7 (Sievers et al., Blood (1999) 93(11): 3678-3684). In some embodiments, the antigen binding fragment for CD38 may comprise the CDRs, light and heavy chain variable domains or other CD38 binding fragment of e.g. anti-CD38 antibody daratumumab (Darzalex), SAR650984 (Martin et al., J Clin Oncol (2014) 32:5s, (suppl; abstr 8532) or MOR202 (MorphoSys AG), or anti-CD38 antibodies described in WO 2006099875 or US 20100285004. In some embodiments, the antigen binding fragment for CD20 may comprise the CDRs, light and heavy chain variable domains or other CD20 binding fragment of e.g. anti-CD20 antibody rituximab, ocrelizumab, ofatumumab, obinutuzumab or BM-ca (Kobayashi et al., Cancer Med (2013) 2(2): 130-143). In some embodiments, the antigen binding fragment for CD24 may comprise the CDRs, light and heavy chain variable domains or other CD24 binding fragment of e.g. anti-CD24 antibody clone eBioSN3 (eBioscience), clone ML5 (BD Biosciences), or anti-CD24 antibodies described in WO 2008059491. In some embodiments, the antigen binding fragment for CD90 may comprise the CDRs, light and heavy chain variable domains or other CD90 binding fragment of e.g. anti-CD90 antibody clone 5E10 (BD Biosciences). In some embodiments, the antigen binding fragment for CD15 may comprise the CDRs, light and heavy chain variable domains or other CD15 binding fragment of e.g. anti-CD15 antibody clone C3D-1, Carb-3 (DAKO A/S), MMA (Roche) or BY87 (Abcam). In some embodiments, the antigen binding fragment for CD52 may comprise the CDRs, light and heavy chain variable domains or other CD52 binding fragment of e.g. anti-CD52 antibody alemtuzumab, clone HI186, or clone YTH34.5 (AbD Serotec). In some embodiments, the antigen binding fragment for CA-125 may comprise the CDRs, light and heavy chain variable domains or other CA-125 binding fragment of e.g. anti-CA-125 antibody oregovomab. In some embodiments, the antigen binding fragment for CD34 may comprise the CDRs, light and heavy chain variable domains or other CD34 binding fragment of e.g. anti-CD34 antibody clone 561 (BioLegend), clone 581 (Beckton Dickinson), or clone 5F3 (Sigma Aldrich). In some embodiments, the antigen binding fragment for CA-15-3 may comprise the CDRs, light and heavy chain variable domains or other CA-15-3 binding fragment of e.g. anti-CA-15-3 antibody clone 2F16 (USBiological), clone TA998 (ThermoFisher Scientific), clone 1D1 (Sigma Aldrich), or Mab AR20.5 (Qi et al., Hybrid Hybridomics (2001) 20(5-6): 313-324). In some embodiments, the antigen binding fragment for CA-19-9 may comprise the CDRs, light and heavy chain variable domains or other CA-19-9 binding fragment of e.g. anti-CA-19-9 antibody clone 116-NS-19-9 (DAKO A/S), clone SPM110, or clone 121SLE (ThermoFisher Scientific). In some embodiments, the antigen binding fragment for CEA may comprise the CDRs, light and heavy chain variable domains or other CEA binding fragment of e.g. anti-CEA antibody labetuzumab, C2-45 (Kyowa Hakko Kirin Co. Ltd.) or anti-CEA antibodies disclosed in Imakiire et al., Int J Cancer (2004) 108: 564-570 or WO 2011034660. In some embodiments, the antigen binding fragment for CD99 may comprise the CDRs, light and heavy chain variable domains or other CD99 binding fragment of e.g. anti-CD99 antibody clone C7A (Moricoli et al., J Immunol Methods (2014) 408: 35-45) or clone 12E7 (DAKO A/S). In some embodiments, the antigen binding fragment for CD117 may comprise the CDRs, light and heavy chain variable domains or other CD117 binding fragment of e.g. anti-CD117 antibody clone CK6 (Lebron et al., Cancer Biol Ther (2014) 15(9): 1208-1218), or clone 104D2 (Sigma Aldrich). In some embodiments, the antigen binding fragment for CD31 may comprise the CDRs, light and heavy chain variable domains or other CD31 binding fragment of e.g. anti-CD31 antibody clone JC70A (DAKO A/S). In some embodiments, the antigen binding fragment for CD44 may comprise the CDRs, light and heavy chain variable domains or other CD44 binding fragment of e.g. anti-CD44 antibody PF-03475952 (Runnels et al., Adv Ther (2010); 27(3): 168-180), RG7356 (Vugts et al., MAbs (2014) 6(2): 567-575), clone IM7, or clone A3D8 (Sigma Aldrich). In some embodiments, the antigen binding fragment for CD123 may comprise the CDRs, light and heavy chain variable domains or other CD123 binding fragment of e.g. anti-CD123 antibody CSL362 (Nievergall et al., Blood (2014) 123(8):1218-1228), CSL360 (He et al., Leuk Lymphoma (2015) 56(5): 1406-1415) 73G (Jin et al., Cell Stem Cell (2009) 5(1): 31-42) clone 6H6 (AbD Serotec) or anti-CD123 antibodies described in WO 2014130635. In some embodiments, the antigen binding fragment for CD133 may comprise the CDRs, light and heavy chain variable domains or other CD133 binding fragment of e.g. anti-CD133 antibody clone 6B3, clone 9G4, clone AC141 (Wang et al., Hybridoma (Larchmt) (2010) 29(3): 241-249), clone 6B6 (Chen et al., Hybridoma (Larchmt) (2010) 29(4): 305-310, clone AC113 (Miltenyi Biotec), or anti-CD133 antibodies described in WO 2011149493. In some embodiments, the antigen binding fragment for ABCB5 may comprise the CDRs, light and heavy chain variable domains or other ABCB5 binding fragment of e.g. anti-ABCB5 antibody clone 5H3C6 (Thermo Fisher Scientific). In some embodiments, the antigen binding fragment for CD45 may comprise the CDRs, light and heavy chain variable domains or other CD45 binding fragment of e.g. anti-CD45 antibody YAML568 (Glatting et al., J Nucl Med (2006) 47(8): 1335-1341) or clone BRA-55 (Sigma Aldrich).

An antigen binding fragment of a bispecific antibody or bispecific antigen binding fragment according to the present invention may be any fragment of a polypeptide which is capable of binding to an antigen. In some embodiments, an antigen binding fragment comprises at least the three light chain CDRs (i.e. LC-CDR1, LC-CDR2 and LC-CDR3) and three heavy chain CDRs (i.e. HC-CDR1, HC-CDR2 and HC-CDR3) which together define the antigen binding region of an antibody or antigen binding fragment. In some embodiments, an antigen binding fragment may comprise the light chain variable domain and heavy chain variable domain of an antibody or antigen binding fragment. In some embodiments, an antigen binding fragment may comprise the light chain polypeptide and heavy chain polypeptide of an antibody or antigen binding fragment.

Bispecific antibodies and bispecific antigen binding fragments according to the invention may be provided in any suitable format, such as those formats described in Kontermann MAbs 2012, 4(2): 182-197, which is hereby incorporated by reference in its entirety. For example, a bispecific antibody or bispecific antigen binding fragment may be a bispecific antibody conjugate (e.g. an IgG2, F(ab')$_2$ or CovX-Body), a bispecific IgG or IgG-like molecule (e.g. an IgG, scFv$_4$-Ig, IgG-scFv, scFv-IgG, DVD-Ig, IgG-sVD, sVD-IgG, 2 in 1-IgG, mAb$^2$, or Tandemab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (Db), dsDb, DART, scDb, tand-Abs, tandem scFv (taFv), tandem dAb/VHH, triple body, triple head, Fab-scFv, or F(ab')$_2$-scFv$_2$), a bispecific Fc and C$_H$3 fusion protein (e.g. a taFv-Fc, Di-diabody, scDb-C$_H$3, scFv-Fc-scFv, HCAb-VHH, scFv-kih-Fc, or scFv-kih-C$_H$3), or a bispecific fusion protein (e.g. a scFv$_2$-albumin, scDb-albumin, taFv-toxin, DNL-Fab$_3$, DNL-Fab$_4$-IgG, DNL-Fab$_4$-IgG-cytokine$_2$). See in particular FIG. 2 of Kontermann MAbs 2012, 4(2): 182-19.

The skilled person is able to design and prepare bispecific antibodies and bispecific antigen binding fragments according to the present invention.

Methods for producing bispecific antibodies include chemically crosslinking of antibodies or antibody fragments, e.g. with reducible disulphide or non-reducible thioether bonds, for example as described in Segal and Bast, 2001. Production of Bispecific Antibodies. Current Protocols in Immunology. 14:IV:2.13:2.13.1-2.13.16, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific F(ab)$_2$ heterodimers.

Other methods for producing bispecific antibodies include fusing antibody-producing hybridomas e.g. with polyethylene glycol, to produce a quadroma cell capable of secreting bispecific antibody, for example as described in D. M. and Bast, B. J. 2001. Production of Bispecific Antibodies. Current Protocols in Immunology. 14:IV:2.13:2.13.1-2.13.16.

Bispecific antibodies and bispecific antigen binding fragments according to the present invention can also be produced recombinantly, by expression from e.g. a nucleic acid construct encoding polypeptides for the antigen binding molecules, for example as described in Antibody Engineering: Methods and Protocols, Second Edition (Humana Press, 2012), at Chapter 40: Production of Bispecific Antibodies: Diabodies and Tandem scFv (Hornig and Frber-Schwarz), or French, How to make bispecific antibodies, Methods Mol. Med. 2000; 40:333-339, the entire contents of both of which are hereby incorporated by reference. For example, a DNA construct encoding the light and heavy chain variable domains for the two antigen binding fragments (i.e. the light and heavy chain variable domains for the antigen binding fragment capable of binding PD-L1, and the light and heavy chain variable domains for the antigen binding fragment capable of binding to another target protein), and including sequences encoding a suitable linker or dimerization domain between the antigen binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

Antibodies may be produced by a process of affinity maturation in which a modified antibody is generated that has an improvement in the affinity of the antibody for antigen, compared to an unmodified parent antibody. Affinity-matured antibodies may be produced by procedures known in the art, e.g., Marks et al., *Bio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):331 0-15 9 (1995); and Hawkins et al, *J. Mol. Biol.* 226:889-896 (1992).

Antibodies according to the present invention preferably exhibit specific binding to PD-L1. An antibody that specifically binds to a target molecule preferably binds the target with greater affinity, and/or with greater duration than it binds to other targets. The present antibodies may bind with greater affinity to PD-L1 than to another member of the CD28 family. In some embodiments the present antibodies may bind with greater affinity to PD-L1 than to one or more of PD-L2, TIM-3, LAG-3, ICOS, BTLA, CD28 or CTLA-4. In one embodiment, the extent of binding of an antibody to an unrelated target is less than about 10% of the binding of the antibody to the target as measured, e.g., by ELISA, or by a radioimmunoassay (RIA). Alternatively, the binding specificity may be reflected in terms of binding affinity where the anti-PD-L1 antibody of the present invention binds to PD-L1 with a $K_D$ that is at least 0.1 order of magnitude (i.e. $0.1 \times 10^n$, where n is an integer representing the order of magnitude) greater than the $K_D$ of the antibody towards another target molecule, e.g. another member of the CD28 family. This may optionally be one of at least 0.2, 0.3, 0.4, 0.5, 0.6, 0.7, 0.8, 0.9, 1.0, 1.5, or 2.0.

Antibodies according to the present invention preferably have a dissociation constant ($K_D$) of one of ≤10 nM, ≤1 nM ≤500 pM, ≤400 pM or ≤300 pM. The $K_D$ may be in the range about 0.1 to about 4 nM. Binding affinity of an antibody for its target is often described in terms of its dissociation constant ($K_D$). Binding affinity can be measured by methods known in the art, such as by Surface Plasmon Resonance (SPR), or by a radiolabeled antigen binding assay (RIA) performed with the Fab version of the antibody and antigen molecule.

Antibodies according to the present invention preferably exhibit binding to PD-L1 (e.g. human PD-L1) with greater affinity than, or with similar affinity to, affinity of binding by atezolizumab (MPDL3280A; RG7446).

As used herein, an antibody displaying 'greater affinity' for a given target molecule compared to a reference antibody binds to that target molecule with greater strength as compared to the strength of binding of the reference antibody to the target molecule. The affinity of an antibody for a given target molecule can be determined quantitatively.

Relative affinity of binding of an antibody according the invention to PD-L1 compared to atezolizumab can be determined for example by ELISA, as described herein. In some embodiments, an antibody according to the present invention may have a dissociation constant ($K_D$) for PD-L1 which is less than or equal to the $K_D$ of atezolizumab for PD-L1.

In some embodiments, an antibody according the present invention may have affinity for PD-L1 which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than the affinity of atezolizumab for PD-L1, in a given assay. In some embodiments, an antibody according the present invention may bind to PD-L1 with a $K_D$ value which is 0.99 times or less, 0.95 times or less, 0.9 times or less, 0.85 times or less, 0.8 times or less, 0.75 times or less, 0.7 times or less, 0.65 times or less, 0.6 times or less, 0.55 times or less, 0.5 times or less of the $K_D$ value of atezolizumab for PD-L1, in a given assay.

Antibodies according to the present invention preferably exhibit binding to PD-L1 (e.g. human PD-L1) with greater avidity than, or with similar avidity to, avidity of binding by atezolizumab.

As used herein, an antibody displaying 'greater avidity' for a given target molecule compared to a reference antibody binds to that target molecule to form a stronger antibody:target complex (e.g. a more stable antibody:target complex) as compared to the antibody:target complex formed by binding of the reference antibody to the target molecule. Avidity of an antibody for a given target molecule can be determined quantitatively.

Relative avidity of binding of an antibody according the invention to PD-L1 compared to atezolizumab can be determined for example by ELISA, as described herein. In some embodiments, an antibody according to the present invention may have an avidity of binding for PD-L1 which is greater than or equal to the avidity of binding of atezolizumab for PD-L1.

In some embodiments, an antibody according the present invention may have avidity of binding for PD-L1 which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than avidity of binding of atezolizumab for PD-L1, in a given assay.

Antibodies according to the present invention preferably inhibit or prevent interaction between PD-L1 and PD-1 (e.g. human PD-L1 and human PD-1) to a greater extent than, or to a similar extent to, inhibition/prevention of interaction between PD-L1 and PD-1 by atezolizumab. Relative inhibition/prevention of interaction between PD-L1 and PD-1 of an antibody according the invention for PD-L1 compared to atezolizumab can be determined for example by ELISA, as described herein. In some embodiments, an antibody according to the present invention may inhibit/prevent interaction between PD-L1 and PD-1 to an extent which is greater than or equal to inhibition/prevention of interaction between PD-L1 and PD-1 by atezolizumab. In some embodiments, an antibody according the present invention may inhibit/prevent interaction between PD-L1 and PD-1 to an extent which is 1.01 times or greater, 1.05 times or greater, 1.1 times or greater, 1.15 times or greater, 1.2 times or greater, 1.25 times or greater, 1.3 times or greater, 1.35 times or greater, 1.4 times or greater, 1.45 times or greater, 1.5 times or greater than inhibition/prevention of interaction between PD-L1 and PD-1 by atezolizumab, in a given assay.

In some embodiments, an antibody according the present invention may inhibit/prevent interaction between PD-L1 and PD-1 with a value for half maximal inhibition of interaction (i.e. an $IC_{50}$ value for inhibition of interaction between PD-L1 and PD-1) which is lower than the $IC_{50}$ value for inhibition of interaction between PD-L1 and PD-1 by atezolizumab. In some embodiments, an antibody according the present invention may inhibit/prevent interaction between PD-L1 and PD-1 with an $IC_{50}$ value which is 0.99 times or less, 0.95 times or less, 0.9 times or less, 0.85 times or less, 0.8 times or less, 0.75 times or less, 0.7 times or less, 0.65 times or less, 0.6 times or less, 0.55 times or less, 0.5 times or less of the $IC_{50}$ value for inhibition of interaction between PD-L1 and PD-1 by atezolizumab, in a given assay.

Antibodies according to the present invention may be "antagonist" antibodies that inhibit or reduce a biological activity of the antigen to which it binds. Blocking of interaction between PD-1 and PD-L1 assists in the restoration of T-cell function by inhibiting the immune-inhibitory signalling pathway mediated by PD-1.

PD-L1 has also been shown to bind to B7-1 (CD80), an interaction that also suppresses T-cell proliferation and cytokine production.

In some aspects, the antibody is clone A1, or a variant of A1. A1 comprises the following CDR sequences:
Light Chain:
  LC-CDR1: SGRSSNIASHDVF (SEQ ID NO:9)
  LC-CDR2: ETNKRPW (SEQ ID NO:10)
  LC-CDR3: GAWDSGLTGML (SEQ ID NO:11)
Heavy Chain:
  HC-CDR1: SYAIS (SEQ ID NO:21)
  HC-CDR2: RIIPILGIANYAQKFQG (SEQ ID NO:22)
  HC-CDR3: GGSYGSLYAFDI (SEQ ID NO:23).
  CDR sequences determined by Kabat definition.

In some aspects, the antibody is clone C2, or a variant of C2. C2 comprises the following CDR sequences:
Light Chain:
  LC-CDR1: GGDNIGRKSVH (SEQ ID NO:12)
  LC-CDR2: DDGDRPS (SEQ ID NO:13)
  LC-CDR3: QAWDSTVV (SEQ ID NO:14)
Heavy Chain:
  HC-CDR1: SYAIS (SEQ ID NO:21)
  HC-CDR2: RIIPILGIANYAQKFQG (SEQ ID NO:22)
  HC-CDR3: GGSYGSLYAFDI (SEQ ID NO:23).
  CDR sequences determined by Kabat definition.

In some aspects, the antibody is clone C4, or a variant of C4. C4 comprises the following CDR sequences:
Light Chain:
  LC-CDR1: SGSSSNIGNNYVS (SEQ ID NO:15)
  LC-CDR2: DNNERLS (SEQ ID NO:16)
  LC-CDR3: GTWDSSLSVVV (SEQ ID NO:17)
Heavy Chain:
  HC-CDR1: SYAIS (SEQ ID NO:21)
  HC-CDR2: RIIPILGIANYAQKFQG (SEQ ID NO:22)
  HC-CDR3: GGYGGNSLYAFDI (SEQ ID NO:24).
  CDR sequences determined by Kabat definition.

In some aspects, the antibody is clone H12, or a variant of H12. In some aspects, the antibody is clone H12_GL, or a variant of H12_GL. H12 and H12_GL each comprise the following CDR sequences:
Light Chain:
  LC-CDR1: TGSSSNIGAGYDVH (SEQ ID NO:18)
  LC-CDR2: GNSNRPS (SEQ ID NO:19)
  LC-CDR3: QSYDSSLSGSYVV (SEQ ID NO:20)
Heavy Chain:
  HC-CDR1: SYAIS (SEQ ID NO:21)
  HC-CDR2: RIIPILGIANYAQKFQG (SEQ ID NO:22)
  HC-CDR3: SGHGYSYGAFDY (SEQ ID NO:25).
  CDR sequences determined by Kabat definition.

Antibodies according to the present invention may comprise the CDRs of A1, C2, C4, H12, or H12_GL or one of SEQ ID NOs 1 and 5; 2 and 6; 3 and 7; 4 and 8; or 4 and 35. In an antibody according to the present invention one or two or three or four of the six CDR sequences may vary. A variant may have one or two amino acid substitutions in one or two of the six CDR sequences.

Amino acid sequences of the $V_H$ and $V_L$ chains of anti-PD-L1 clones are shown in FIGS. 1A-B and 2A-C. The encoding nucleotide sequences are shown in FIGS. 4A-D.

The light and heavy chain CDRs may also be particularly useful in conjunction with a number of different framework regions. Accordingly, light and/or heavy chains having LC-CDR1-3 or HC-CDR1-3 may possess an alternative framework region. Suitable framework regions are well known in the art and are described for example in M. Lefranc & G. Le:franc (2001) "The Immunoglobulin Facts-Book", Academic Press, incorporated herein by reference.

In this specification, antibodies may have $V_H$ and/or $V_L$ chains comprising an amino acid sequence that has a high percentage sequence identity to one or more of the $V_H$ and/or $V_L$ amino acid sequences of SEQ ID NOs 1 and 5; 2 and 6; 3 and 7; 4 and 8; or 4 and 35, or to one or the amino acid sequences shown in FIGS. 1A-B and 2A-C.

For example, antibodies according to the present invention include antibodies that bind PD-L1 and have a $V_H$ or $V_L$ chain that comprises an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to the $V_H$ or $V_L$ chain amino acid sequence of one of SEQ ID NOs 1 to 8 and 35, or to one or the amino acid sequences shown in FIGS. 1A-B and 2A-C.

Antibodies according to the present invention may be detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The binding moiety may be directly labelled with a detectable label or it may be indirectly labelled. For example, the binding moiety may be an unlabelled antibody which can be detected by another antibody which is itself labelled. Alternatively, the second antibody may have bound to it biotin and binding of labelled streptavidin to the biotin is used to indirectly label the first antibody.

Methods of Detection

Antibodies, or antigen binding fragments, described herein may be used in methods that involve the binding of the antibody or antigen binding fragment to PD-L1. Such methods may involve detection of the bound complex of antibody, or antigen binding fragment, and PD-L1. As such, in one embodiment a method is provided, the method comprising contacting a sample containing, or suspected to contain, PD-L1 with an antibody or antigen binding fragment as described herein and detecting the formation of a complex of antibody, or antigen binding fragment, and PD-L1.

Suitable method formats are well known in the art, including immunoassays such as sandwich assays, e.g. ELISA. The method may involve labelling the antibody, or antigen binding fragment, or PD-L1, or both, with a detectable label, e.g. fluorescent, luminescent or radio-label. PD-L1 expression may be measured by immunohistochemistry (IHC), for example of a tissue sample obtained by biopsy.

Methods of this kind may provide the basis of a method of diagnosis of a disease or condition requiring detection and or quantitation of PD-L1 or PD-1. Such methods may be performed in vitro on a patient sample, or following processing of a patient sample. Once the sample is collected, the patient is not required to be present for the in vitro method of diagnosis to be performed and therefore the method may be one which is not practised on the human or animal body.

Such methods may involve determining the amount of PD-L1 present in a patient sample. The method may further comprise comparing the determined amount against a standard or reference value as part of the process of reaching a diagnosis. Other diagnostic tests may be used in conjunction with those described here to enhance the accuracy of the diagnosis or prognosis or to confirm a result obtained by using the tests described here.

Cancer cells may exploit the PD-1 pathway to create an immunosuppressive environment, by upregulating expression of PD-L1 and/or PD-1, allowing activation of the inhibitory PD-1 receptor on any T cells that infiltrate the tumor microenvironment and thereby suppressing their activity. Upregulation of PD-L1 and/or PD-1 expression has been demonstrated in many different cancer types, and high PD-L1/PD-1 expression has also been linked to poor clinical outcomes.

The level of PD-L1 or PD-1 present in a patient sample may be indicative that a patient may respond to treatment with an anti-PD-L1 antibody. The presence of a high level of PD-L1 or PD-1 in a sample may be used to select a patient for treatment with an anti-PD-L1 antibody. The antibodies of the present invention may therefore be used to select a patient for treatment with anti-PD-L1 therapy.

Detection in a sample of PD-L1 or PD-1 may be used for the purpose of diagnosis of a T-cell dysfunctional disorder or a cancerous condition in the patient, diagnosis of a predisposition to a cancerous condition or for providing a prognosis (prognosticating) of a cancerous condition. The diagnosis or prognosis may relate to an existing (previously diagnosed) cancerous condition, which may be benign or malignant, may relate to a suspected cancerous condition or may relate to the screening for cancerous conditions in the patient (which may be previously undiagnosed).

In one embodiment the level of PD-1 expression on CD8+ T cells may be detected in order to indicate the degree of T-cell exhaustion and severity of the disease state.

In one embodiment the level of PD-L1 expression, e.g. on antigen presenting cells or tumor cells, may be detected in order to indicate existence or severity of a disease state, for example of tissue inflammation or a cancer.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; or cells isolated from said individual.

Methods according to the present invention are preferably performed in vitro. The term "in vitro" is intended to encompass experiments with cells in culture whereas the term "in vivo" is intended to encompass experiments with intact multi-cellular organisms.

Therapeutic Applications

Antibodies, antigen binding fragments and polypeptides according to the present invention and compositions comprising such agents may be provided for use in methods of medical treatment. Treatment may be provided to subjects having a disease or condition in need of treatment. The disease or condition may be one of a T-cell dysfunctional disorder, including a T-cell dysfunctional disorder associated with a cancer, or a cancer, or a T-cell dysfunctional disorder associated with an infection, or an infection.

A T-cell dysfunctional disorder may be a disease or condition in which normal T-cell function is impaired causing downregulation of the subject's immune response to pathogenic antigens, e.g. generated by infection by exogenous agents such as microorganisms, bacteria and viruses, or generated by the host in some disease states such as in some forms of cancer (e.g. in the form of tumor associated antigens).

The T-cell dysfunctional disorder may comprise T-cell exhaustion or T-cell anergy. T-cell exhaustion comprises a state in which CD8$^+$ T-cells fail to proliferate or exert T-cell effector functions such as cytotoxicity and cytokine (e.g. IFNγ) secretion in response to antigen stimulation. Exhausted T-cells may also be characterised by sustained expression of PD-1, where blockade of PD-1:PD-L1 interactions may reverse the T-cell exhaustion and restore antigen-specific T cell responses.

The T-cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with Helicobacterpylori. Examples of viral infections include infection with HIV, hepatitis B or hepatitis C.

The T-cell dysfunctional disorder may be associated with a cancer, such as tumor immune escape. Many human tumors express tumor-associated antigens recognised by T cells and capable of inducing an immune response. However, immune evasion is common and is believed to be mediated by a number of soluble factors, including PD-L1. As such, blocking the interaction of PD-1 and PD-L1 may inhibit this negative immunoregulatory signal to tumor cells and enhance tumor-specific CD8$^+$ T-cell immunity.

Cancers may also be treated where there is no indication of a T-cell dysfunctional disorder such as T-cell exhaustion but the use of an antibody, antigen binding fragment or polypeptide according to the present invention allows the subject to suppress PD-1 signalling and mount an effective immune response with limited impairment, evasion or induction of tumor immune escape. In such treatments, the antibody, antigen binding fragment or polypeptide may provide a treatment for cancer that involves prevention of the development of tumor immune escape.

Cancers may also be treated which overexpress PD-L1. For example, such tumor cells overexpressing PD-L1 may be killed directly by treatment with anti-PD-L1 antibodies, by antibody dependent cell-mediated cytotoxicity (ADCC), complement dependent cytotoxicity (CDC), or using anti-PD-L1 antibody-drug conjugates.

The treatment may be aimed at prevention of the T-cell dysfunctional disorder, e.g. prevention of infection or of the development or progression of a cancer. As such, the antibodies, antigen binding fragments and polypeptides may be used to formulate pharmaceutical compositions or medicaments and subjects may be prophylactically treated against development of a disease state. This may take place before the onset of symptoms of the disease state, and/or may be given to subjects considered to be at greater risk of infection or development of cancer.

Treatment may comprise co-therapy with a vaccine, e.g. T-cell vaccine, which may involve simultaneous, separate or sequential therapy, or combined administration of vaccine and antibody, antigen binding fragment or polypeptide in a single composition. In this context, the antibody, antigen binding fragment or polypeptide may be provided as an adjuvant to the vaccine. Limited proliferative potential of exhausted T cells has been attributed as a main reason for failure of T-cell immunotherapy and combination an agent capable of blocking or reversing T cell exhaustion is a potential strategy for improving the efficacy of T-cell immunotherapy (Barber et al., *Nature* Vol 439, No. 9 p 682-687 February 2006).

Administration of an antibody, antigen binding fragment or polypeptide is preferably in a "therapeutically effective amount", this being sufficient to show benefit to the individual. The actual amount administered, and rate and timecourse of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

Formulating Pharmaceutically Useful Compositions and Medicaments

Antibodies, antigen binding fragments and polypeptides according to the present invention may be formulated as pharmaceutical compositions for clinical use and may comprise a pharmaceutically acceptable carrier, diluent, excipient or adjuvant.

In accordance with the present invention methods are also provided for the production of pharmaceutically useful compositions, such methods of production may comprise one or more steps selected from: isolating an antibody, antigen binding fragment or polypeptide as described herein; and/or mixing an isolated antibody, antigen binding fragment or polypeptide as described herein with a pharmaceutically acceptable carrier, adjuvant, excipient or diluent.

For example, a further aspect of the present invention relates to a method of formulating or producing a medicament or pharmaceutical composition for use in the treatment of a T-cell dysfunctional disorder, the method comprising formulating a pharmaceutical composition or medicament by mixing an antibody, antigen binding fragment or polypeptide as described herein with a pharmaceutically acceptable carrier, adjuvant, excipient or diluent.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry *Nature Immunology* Vol. 12, No. 6, p 492-499, June 2011).

An infection or infectious disease may be one in which PD-1 is upregulated (e.g. as reported by Radziewicz H, et al., J Virol. 2007; 81(6):2545-2553 and Golden-Mason L et al., J Virol. 2007; 81(17):9249-9258), thereby also implicating the PD-1:PD-L1 interaction as part of the disease state.

Examples of bacterial infections that may be treated include infection by *Bacillus* spp., *Bordetella pertussis*, *Clostridium* spp., *Corynebacterium* spp., *Vibrio chloerae*, *Staphylococcus* spp., *Streptococcus* spp. *Escherichia*, *Klebsiella*, *Proteus*, *Yersinia*, *Erwina*, *Salmonella*, *Listeria* sp, *Helicobacter pylori*, mycobacteria (e.g. *Mycobacterium tuberculosis*) and *Pseudomonas aeruginosa*. For example, the bacterial infection may be sepsis or tuberculosis.

Yao et al. (PD-1 on dendritic cells impedes innate immunity against bacterial infection. *Blood* 113(23):5811-5818 Jun. 4 2009) established PD-1 in the negative regulation of DC function during innate immune response to infection by *Listeria monocytogenes*. Brahmamdam et al (Delayed administration of anti-PD-1 antibody reverses immune dysfunction and improves survival during sepsis. *Journal of Leukocyte Biology* vo. 88, no. 2 233-240, August 2010) reported that anti-PD-1 antibody administered 24 h after sepsis prevented sepsis-induced depletion of lymphocytes and DCs, increased Bcl-xL, blocked apoptosis and improved survival. Tim3:Galectin-9 interactions have been reported to mediate T cell exhaustion and mediate the innate and adaptive immune response to infection by *Mycobacterium tuberculosis* (Jayaraman et al., *The Journal of Immunology* 2012, 188, 70.6).

Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus.

Chronic viral infections, such as those caused by HCV, HBV, and HIV commonly involve mechanisms to evade immune clearance. Expression of PD-1 and TIM-3 have been identified as correlating with defective T cell responses to hepatitis C virus (HCV) (McMahan et al., The Journal of Clinical Investigation Vol. 120, No. 12 p 4546-4557, December 2010). In HCV, McMahan et al (supra) found that the level of dual TIM-3 and PD-1 expression on HCV-specific CTLs predated the development of viral persistence, providing prognostic information. Barber et al. (Nature Vol 439, No. 9 p 682-687 February 2006) reported that PD-1 is upregulated during chronic viral infection. In mice infected with LCMV they reported that blockade of the PD-1/PD-L1 inhibitory pathway had a beneficial effect on CD8 T cells, restoring their ability to undergo proliferation, secrete cytokines, kill infected cells and decrease viral load. PD-1 is also upregulated in HIV infection (Said et al., *Nature Medicine* Vol. 16, No. 4 p 452-460 April 2010). Blocking interaction between PD-1 and PD-L1 contributed to viral clearance and improved T cell function in animal models of chronic viral infection (Said et al., supra).

Examples of fungal infections that may be treated include infection by *Alternaria* sp, *Aspergillus* sp, *Candida* sp and *Histoplasma* sp. The fungal infection may be fungal sepsis or histoplasmosis.

Chang et al (Blockade of the negative co-stimulatory molecules PD-1 and CTLA-4 improves survival in primary and secondary fungal sepsis. *Critical Care* 2013, 17:R85) reported that anti-PD1 antibodies were highly effective at improving survival in primary and secondary fungal sepsis. Lazar-Molnar et al (The PD-1/PD-L costimulatory pathway critically affects host resistance to the pathogenic fungus *Histoplasma capsulatum* PNAS vol. 105, no. 7, p 2658-2663, 19 Feb. 2008) reported that anti-PD-1 antibody significantly increased survival of mice infected with *Histoplasma capsulatum*. As such, the importance of T cell exhaustion in mediating fungal infection is well established.

Examples of parasitic infections that may be treated include infection by *Plasmodium* species (e.g. *Plasmodium falciparum, Plasmodium yoeli, Plasmodium ovale, Plasmodium vivax*, or *Plasmodium chabaudi chabaudi*). The parasitic infection may be a disease such as malaria, leishmaniasis and toxoplasmosis.

Infection of humans with *Plasmodium falciparum* has been shown to result in higher expression of PD-1 and T cell exhaustion mice (Butler et al., *Nature Immunology* Vol. 13, No. 12, p 188-195 February 2012). Blockade of PD-L1 and LAG-3 using anti-PD-L1 and anti-LAG-3 monoclonal antibodies in vivo contributed to the restoration of CD4$^+$ T-cell function, amplification of the number of follicular helper T cells, germinal-center B cells and plasmablasts, enhanced protective antibodies and rapidly cleared blood-stage malaria in mice. It was also shown to block the development of chronic infection (Butler et al., supra).

Cancer

A cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

Adoptive T Cell Transfer Therapy

Adoptive T cell transfer therapy generally refers to a process in which white blood cells are removed from a subject, typically by drawing a blood sample from which white blood cells are separated, expanded in vitro or ex vivo and returned either to the same subject or to a different subject. The treatment is typically aimed at increasing the amount/concentration of an active form of the required T cell population in the subject. Such treatment may be beneficial in subjects experiencing T cell exhaustion.

Antibodies capable of blocking the mechanism of T cell exhaustion, or reversing it, provide a means of enhancing T cell activity and promoting T cell expansion.

Accordingly, in a further aspect of the present invention a method is provided for expanding a population of T cells, wherein T cells are contacted in vitro or ex vivo with an antibody, antigen binding fragment or polypeptide according to the present invention.

The method may optionally comprise one or more of the following steps: taking a blood sample from a subject; isolating T cells from the blood sample; culturing the T cells in in vitro or ex vivo cell culture (where they may be contacted with the antibody, antigen binding fragment or polypeptide), collecting an expanded population of T cells; mixing the T cells with an adjuvant, diluent, or carrier; administering the expanded T cells to a subject.

Accordingly, in some aspects of the present invention a method of treatment of a subject having a T-cell dysfunctional disorder is provided, the method comprising obtaining a blood sample from a subject in need of treatment, culturing T cells obtained from the blood sample in the presence of an antibody, antigen binding fragment or polypeptide according to the present invention so as to expand the T cell population, collecting expanded T cells, and administering the expanded T cells to a subject in need of treatment.

The T cells may be obtained from a subject requiring treatment, and may be isolated and/or purified. They may be a CD4+ and/or CD8$^+$ T-cell population. The T-cells may represent a population experiencing T cell exhaustion and may optionally have upregulated expression of PD-1 and/or PD-L1.

During culture, T cells may be contacted with the antibody, antigen binding fragment or polypeptide under conditions and for a period of time suitable to allow expansion of the T cells to a desired number of cells. After a suitable period of time the T cells may be harvested, optionally concentrated, and may be mixed with a suitable carrier, adjuvant or diluent and returned to the subject's body. A subject may undergo one or more rounds of such therapy.

Methods of T cell expansion are well known in the art, such as those described in Kalamasz et al., *J Immunother* 2004 September-October; 27(5):405-18; Montes et al., *Clin Exp Immunol* 2005 November; 142(2):292-302; Wolfl and Greenburg *Nature Protocols* 9 p 950-966 27 Mar. 2014;

Trickett and Kwan *Journal of Immunological Methods* Vol. 275, Issues 1-2, 1 Apr. 2003, p 251-255; Butler et al *PLoSONE* 7(1) 12 Jan. 2012.

Simultaneous or Sequential Administration

Compositions may be administered alone or in combination with other treatments, either simultaneously or sequentially dependent upon the condition to be treated.

In this specification an antibody, antigen binding fragment or polypeptide of the present invention and an anti-infective agent or chemotherapeutic agent (therapeutic agent) may be administered simultaneously or sequentially.

In some embodiments, treatment with an antibody, antigen binding fragment or polypeptide of the present invention may be accompanied by chemotherapy.

Simultaneous administration refers to administration of the antibody, antigen binding fragment or polypeptide and therapeutic agent together, for example as a pharmaceutical composition containing both agents (combined preparation), or immediately after each other and optionally via the same route of administration, e.g. to the same artery, vein or other blood vessel.

Sequential administration refers to administration of one of the antibody, antigen binding fragment or polypeptide or therapeutic agent followed after a given time interval by separate administration of the other agent. It is not required that the two agents are administered by the same route, although this is the case in some embodiments. The time interval may be any time interval.

Anti-Infective Agents

In treating infection, an antibody, antigen binding fragment or polypeptide of the present invention may be administered in combination with an anti-infective agent, as described above. The anti-infective agent may be an agent known to have action against the microorganism or virus responsible for the infection.

Suitable anti-infective agents include antibiotics (such as penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins), anti-viral agents (such as reverse transcriptase inhibitors, integrase inhibitors, transcription factor inhibitors, antisense and siRNA agents and protease inhibitors), anti-fungal agents (such as polyenes, imidiazoles, triazoles, thiazoles, allylamines, and echinocandins) and anti-parasitic agents (such as antinematode agents, antices-tode agents, antitrematode agents, antiamoebic agents and antiprotozoal agents).

Chemotherapy

Chemotherapy refers to treatment of a cancer with a drug or with ionising radiation (e.g. radiotherapy using X-rays or γ-rays). In preferred embodiments chemotherapy refers to treatment with a drug. The drug may be a chemical entity, e.g. small molecule pharmaceutical, antibiotic, DNA intercalator, protein inhibitor (e.g. kinase inhibitor), or a biological agent, e.g. antibody, antibody fragment, nucleic acid or peptide aptamer, nucleic acid (e.g. DNA, RNA), peptide, polypeptide, or protein. The drug may be formulated as a pharmaceutical composition or medicament. The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from:
  alkylating agents such as cisplatin, carboplatin, mechlorethamine, cyclophosphamide, chlorambucil, ifosfamide;
  purine or pyrimidine anti-metabolites such as azathiopurine or mercaptopurine;
  alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel;
  topoisomerase inhibitors such as the type I topoisomerase inhibitors camptothecins irinotecan and topotecan, or the type II topoisomerase inhibitors amsacrine, etoposide, etoposide phosphate, teniposide;
  antitumor antibiotics (e.g. anthracyline antibiotics) such as dactinomycin, doxorubicin (Adriamycin™), epirubicin, bleomycin, rapamycin;
  antibody based agents, such as anti-PD-1 antibodies, anti-TIM-3 antibodies, anti-CTLA-4, anti-LAG-3, anti-4-1 BB, anti-GITR, anti-CD27, anti-BLTA, anti-OX40, anti-VEGF, anti-TNFα, anti-IL-2, antiGpIIb/IIIa, anti-CD-52, anti-CD20, anti-RSV, anti-HER2/neu(erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab
  EGFR inihibitors such as erlotinib, cetuximab and gefitinib
  anti-angiogenic agents such as bevacizumab (Avastin®)
  cancer vaccines such as Sipuleucel-T (Provenge®)

In one embodiment the chemotherapeutic agent is an anti-PD-1 antibody, anti-TIM-3 antibody, anti-CTLA-4, anti-LAG3, anti-41 BB, anti-GITR, anti-CD27, anti-BLTA, anti-OX40, anti-VEGF, anti-TNFα, anti-1L2, anti-GpIIb/IIIa, anti-CD-52, anti-CD20, anti-RSV, anti-HER2/neu (erbB2), anti-TNF receptor, anti-EGFR or other antibody. In some embodiments, the chemotherapeutic agent is an immune checkpoint inhibitor or costimulation molecule.

Further chemotherapeutic drugs may be selected from: 13-cis-Retinoic Acid, 2-Chlorodeoxyadenosine, 5-Azacitidine 5-Fluorouracil, 6-Mercaptopurine, 6-Thioguanine, Abraxane, Accutane®, Actinomycin-D Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Eligard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte-Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Oprapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Routes of Administration

Antibodies, antigen binding fragments, polypeptides and other therapeutic agents, medicaments and pharmaceutical compositions according to aspects of the present invention may be formulated for administration by a number of routes, including but not limited to, parenteral, intravenous, intraarterial, intramuscular, subcutaneous, intradermal, intratumoral and oral. Antibodies, antigen binding fragments, polypeptides and other therapeutic agents, may be formulated in fluid or solid form. Fluid formulations may be formulated for administration by injection to a selected region of the human or animal body.

Dosage Regime

Multiple doses of the antibody, antigen binding fragment or polypeptide may be provided.

One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

Kits

In some aspects of the present invention a kit of parts is provided. In some embodiments the kit may have at least one container having a predetermined quantity of the antibody, antigen binding fragment or polypeptide. The kit may provide the antibody, antigen binding fragment or polypeptide in the form of a medicament or pharmaceutical composition, and may be provided together with instructions for administration to a patient in order to treat a specified disease or condition. The antibody, antigen binding fragment or polypeptide may be formulated so as to be suitable for injection or infusion to a tumor or to the blood.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition. The therapeutic agent may also be formulated so as to be suitable for injection or infusion to a tumor or to the blood.

Subjects

The subject to be treated may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, or be suspected of having such a disease or condition.

Protein Expression

Molecular biology techniques suitable for producing polypeptides according to the invention in cells are well known in the art, such as those set out in Sambrook et al., Molecular Cloning: A Laboratory Manual, New York: Cold Spring Harbor Press, 1989

The polypeptide may be expressed from a nucleotide sequence. The nucleotide sequence may be contained in a vector present in a cell, or may be incorporated into the genome of the cell.

A "vector" as used herein is an oligonucleotide molecule (DNA or RNA) used as a vehicle to transfer exogenous genetic material into a cell. The vector may be an expression vector for expression of the genetic material in the cell. Such vectors may include a promoter sequence operably linked to the nucleotide sequence encoding the gene sequence to be expressed. A vector may also include a termination codon and expression enhancers. Any suitable vectors, promoters, enhancers and termination codons known in the art may be used to express polypeptides from a vector according to the invention. Suitable vectors include plasmids, binary vectors, viral vectors and artificial chromosomes (e.g. yeast artificial chromosomes).

In this specification the term "operably linked" may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. Where appropriate, the resulting transcript may then be translated into a desired protein or polypeptide.

Any cell suitable for the expression of polypeptides may be used for producing peptides according to the invention. The cell may be a prokaryote or eukaryote. Suitable prokaryotic cells include *E. coli*. Examples of eukaryotic cells include a yeast cell, a plant cell, insect cell or a mammalian cell. In some cases the cell is not a prokaryotic cell because some prokaryotic cells do not allow for the same post-translational modifications as eukaryotes. In addition, very high expression levels are possible in eukaryotes and proteins can be easier to purify from eukaryotes using appropriate tags. Specific plasmids may also be utilised which enhance secretion of the protein into the media.

Methods of producing a polypeptide of interest may involve culture or fermentation of a cell modified to express the polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted polypeptide. Culture, fermentation and separation techniques are well known to those of skill in the art.

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the polypeptide of interest, that polypeptide is preferably isolated. Any suitable method for separating polypeptides/proteins from cell culture known in the art may be used. In order to isolate a polypeptide/protein of interest from a culture, it may be necessary to first separate the cultured cells from media containing the polypeptide/protein of interest. If the polypeptide/protein of interest is secreted from the cells, the cells may be separated from the culture media that contains the secreted polypeptide/protein by centrifugation. If the polypeptide/protein of interest collects within the cell, it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide/protein of interest.

It may then be desirable to isolate the polypeptide/protein of interest from the supernatant or culture medium, which may contain other protein and non-protein components. A common approach to separating polypeptide/protein components from a supernatant or culture medium is by precipitation. Polypeptides/proteins of different solubility are precipitated at different concentrations of precipitating agent such as ammonium sulfate. For example, at low concentrations of precipitating agent, water soluble proteins are extracted. Thus, by adding increasing concentrations of precipitating agent, proteins of different solubility may be distinguished. Dialysis may be subsequently used to remove ammonium sulfate from the separated proteins.

Other methods for distinguishing different polypeptides/proteins are known in the art, for example ion exchange chromatography and size chromatography. These may be used as an alternative to precipitation, or may be performed subsequently to precipitation.

Once the polypeptide/protein of interest has been isolated from culture it may be necessary to concentrate the protein. A number of methods for concentrating a protein of interest are known in the art, such as ultrafiltration or lyophilisation.

Sequence Identity

Alignment for purposes of determining percent amino acid or nucleotide sequence identity can be achieved in various ways known to a person of skill in the art, for instance, using publicly available computer software such as ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

BRIEF DESCRIPTION OF THE FIGURES

Embodiments and experiments illustrating the principles of the invention will now be discussed with reference to the accompanying figures in which:

FIGS. 1A-B. Light chain variable domain sequences for anti-PD-L1 antibody clones A1, C2, C4, H12 and H12_GL. CDRs are underlined and shown separately.

FIGS. 2A-C. Heavy chain variable domain sequences for anti-PD-L1 antibody clones A1, C2, C4, H12 and H12_GL. CDRs are underlined and shown separately.

FIG. 3. Table showing light chain and heavy chain CDR sequences for anti-PD-L1 antibody clones A1, C2, C4, H12 and H12_GL.

FIGS. 4A-D. Nucleotide and encoded amino acid sequences of heavy and light chain variable domain sequences for anti-PD-L1 antibody clones A1, C2, C4, H12 and H12_GL.

(FIG. 18A) and (FIG. 18B) show the results of tumour growth (mean±SEM) for two independent experiments.

(FIG. 19A) Binding of H12, C4, atezolizumab and isotype control antibodies to human PD-L1 (mean±SD of duplicates). (FIG. 19B) Avidity of binding of H12, C4, atezolizumab and isotype control antibodies to human PD-L1 (mean±SD of duplicates).

EXAMPLES

The inventors describe in the following Examples the identification of nucleotide and amino-acid sequences of isolated antibodies, or the antigen-binding portions thereof, that specifically bind human and murine PD-L1, block the PD-1 pathway and restore exhausted T cell activity.

Example 1: Isolation of Anti-Human PD-L1 Antibodies

Anti-PD-L1 antibodies were isolated from a human antibody phage display library via in vitro selection.

Streptavidin-magnetic beads were coated with biotinylated human PD-L1 and used to fish-out anti-PD-L1-specific phages using magnetic sorting. Some steps to remove potential anti-biotin antibodies were added in the selection process.

Specific Fab antibodies were originally identified by ELISA with human-PD-L1 as the antigen. Four clones were retained for further characterisation based on their slow dissociation from human PD-L1: clones A1, C2, C4 and H12. A first clonality screening was performed by DNA fingerprinting; clonality was then confirmed by sequencing.

Example 2: Binding to Human and Murine PD-L1

Human and murine PD-L1 were coupled to human Fc and used as antigens coated on ELISA plates for investigation of antibody binding.

Briefly, ELISA plates were coated with human or murine PD-L1-Fc in carbonate buffer, plates were then blocked with a solution of casein and after extensive washes in PBS Tween-20, anti-PD-L1 antibodies in Fab format were added into the ELISA wells in the presence of 7% milk in PBS. After 90 minutes at room temperature under agitation and extensive washes, a goat anti-human Fab antibody coupled to HRP was added. One hour later, plates were washed and TMB substrate added. The reaction was stopped with 1M HCl and optical density measured at 450 nm with a reference at 670 nm.

Figure 5:
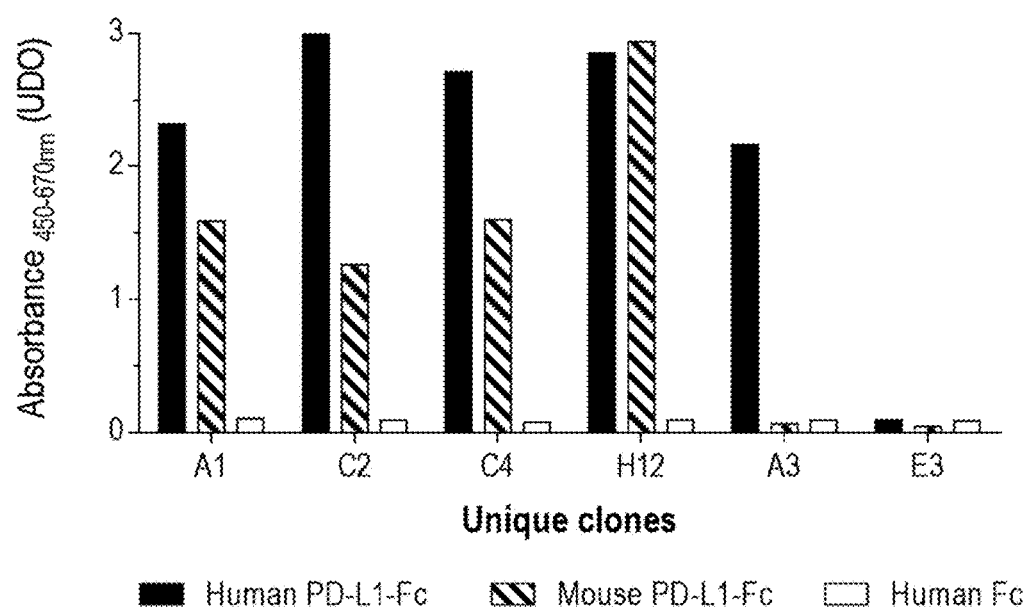
FIG. 5. Bar Chart showing binding of anti-PD-L1, human Fc conjugated antibodies A1, C2, C4 and H12 and control antibodies A3 (which binds to human but not murine PD-L1) and E3 (which does not bind to human or murine PD-L1).

The results are shown in FIG. 5. A1, C2, C4 and H12 antibodies were found to be capable of recognising both human and murine PD-L1 (solid and hatched bars, respectively), and not the coupled Fc part (open bars). Clone A3, which recognises human but not murine PD-L1, and clone E3 which does not recognise either human or murine PD-L1, were included as controls.

Antibody clones A1, C2, C4 and H12 were each found to be cross reactive for human PD-L1 and murine PD-L1. H12 demonstrated similar binding to human PD-L1 and murine PD-L1.

Example 3: Blocking the PD-1/PD-L1 Interaction In Vitro

Anti-PD-L1 antibodies were investigated for their ability to block binding of PD-L1 to PD-1 by ELISA assay using PD-1 coupled to human Fc as an antigen. Biotinylated human or murine PD-L1 was pre-incubated in the presence of A1, C4, C2 or H12 Fab prior to addition onto PD-1. Binding of PD-L1 to PD-1 was determined using streptavidin-HRP/TMB substrate. The results of these investigations are shown in FIGS. 6 and 7.

Figure 6:
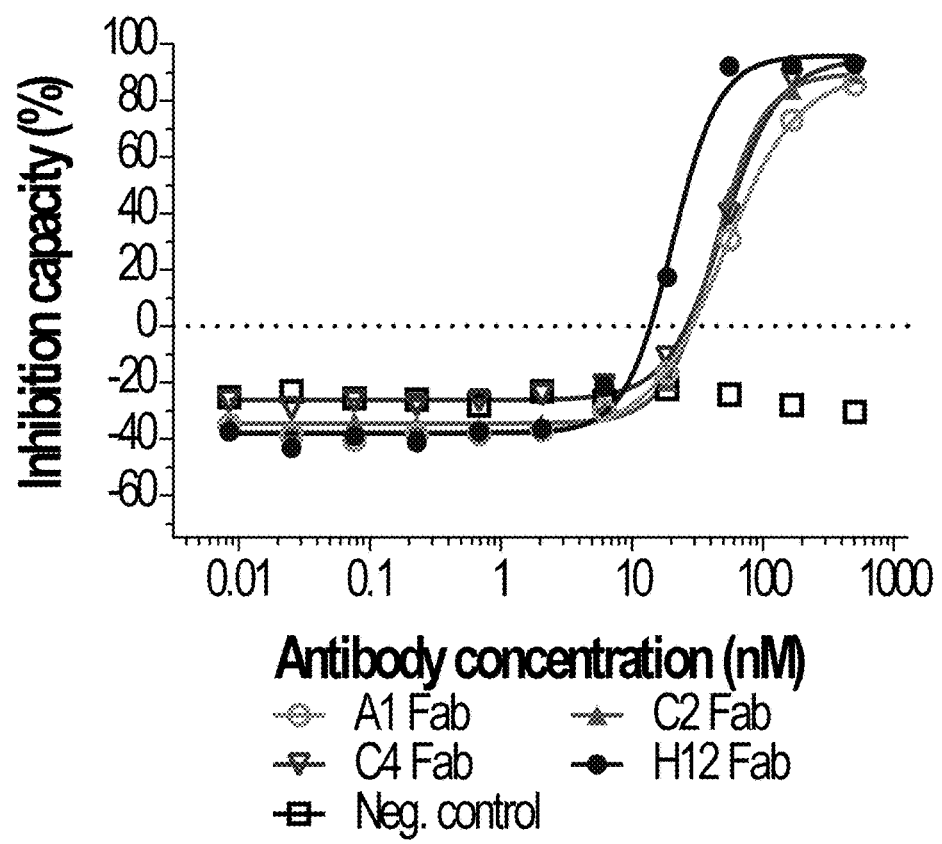
FIG. 6. Chart showing inhibition of human PD-1/human PD-L1 interaction by human Fc conjugated antibodies A1, C2, C4 and H12, as determined by ELISA.

Antibodies A1, C2, C4 and H12 expressed as Fabs were all found to effectively inhibit the binding of human PD-L1 to human PD-1 in a dose-dependent manner (FIG. 6). Clones A1, C2 and C4 were found to inhibit this interaction with similar efficiency, whilst H12 was found to be slightly more effective than A1, C2 and C4 (FIG. 6).

Figure 7:
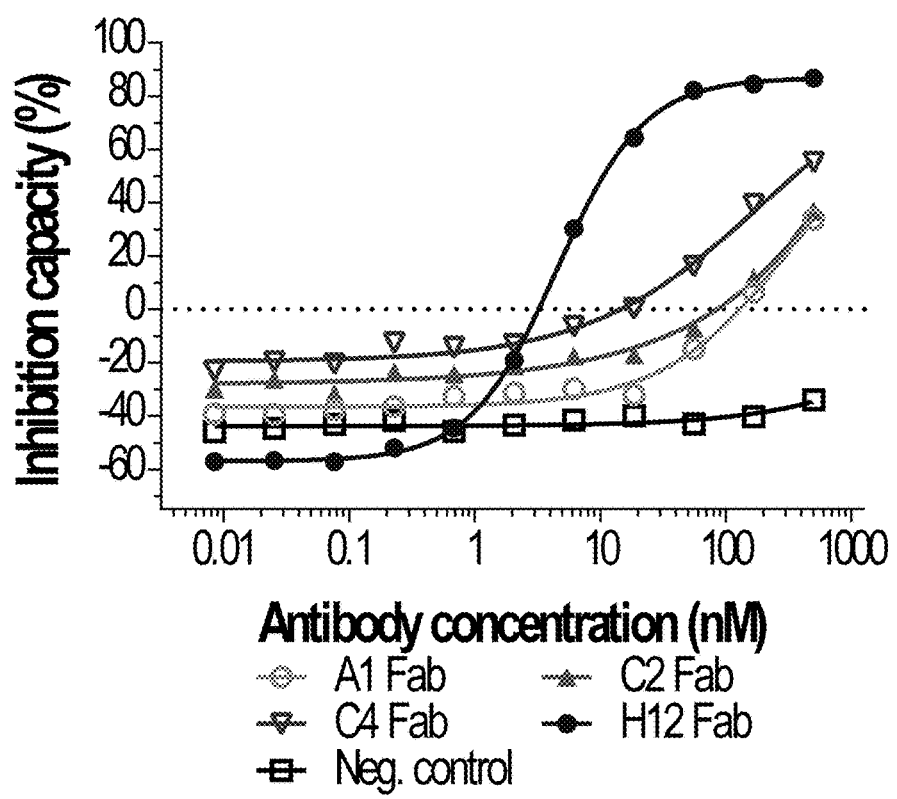
FIG. 7. Chart showing inhibition of murine PD-1/murine PD-L1 interaction by human Fc conjugated antibodies A1, C2, C4 and H12, as determined by ELISA.

Antibody A1, C2, C4 and H12 expressed as Fabs were also found to be able to block the binding of murine PD-L1 to murine PD-1 (FIG. 7). Whilst antibodies A1, C2 and C4 were found to disrupt interaction between murine PD-L1 and murine PD-1 at concentrations higher than the concentration required to block binding of human PD-L1 to human PD-1, H12 was found to be capable of neutralising binding at concentrations similar to those required to block interaction between human PD-L1 and human PD-1 (FIG. 7).

Figure 8:
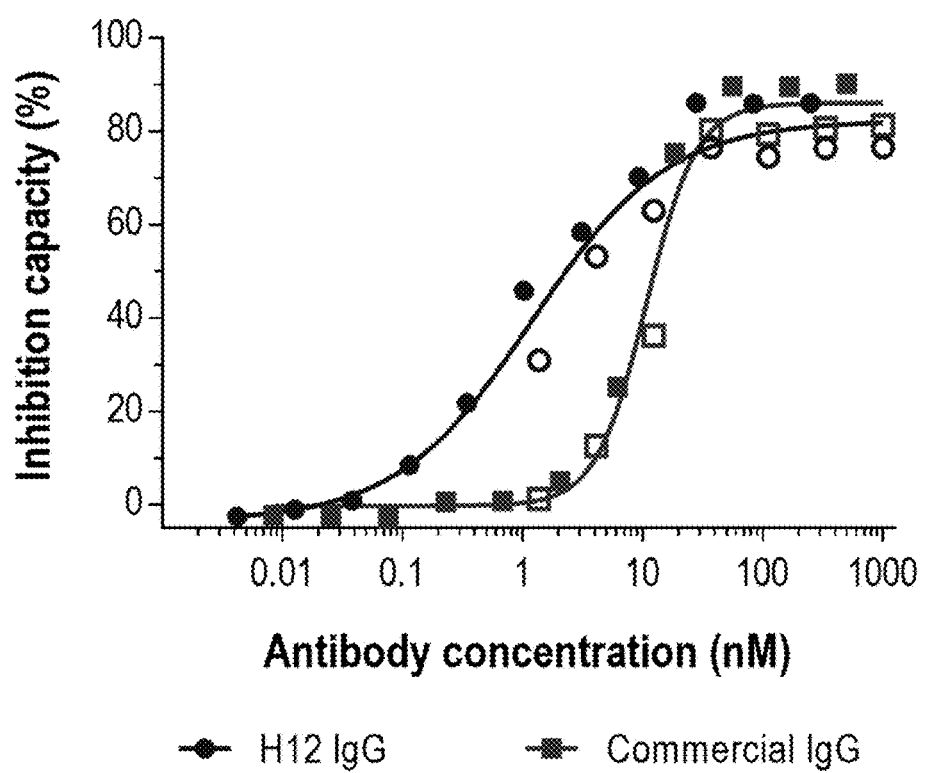
FIG. 8. Chart showing inhibition of murine PD-1/murine PD-L1 interaction by H12 (IgG1) and commercial anti-mouse PD-L1 antibody.

Inhibition of binding between murine PD-L1 and murine PD-1 was also investigated by antibody H12 expressed in the IgG1 format, and compared to inhibition by a commercially available anti-murine PD-L1 IgG antibody [10F.9G2 (BioLegend, Inc, San Diego, Calif., USA)]. The results are shown in FIG. 8. Antibody H12 was found to be significantly more effective at inhibiting interaction between murine PD-L1 and murine PD-1 at lower antibody concentrations as compared to the commercially available anti-murine PD-L1 IgG antibody.

Example 4: Restoration of Exhausted T Cell Activity

Ability of anti-PD-L1 antibody H12 to restore exhausted T cell activity was investigated.

Briefly, T cells were isolated from a healthy donor and cultured for 7 days with monocyte-derived dendritic cells obtained from another donor (50,000 T cells/5,000 DCs), in an allogeneic reaction. The T cells underwent two rounds of stimulation to achieve exhaustion. The exhausted T cells were cultured in the presence of antibody H12 or the anti-PD-1 antibody Nivolumab in the second round of stimulation for 5 days, prior to measurement of IFN-γ in the supernatants and quantification of proliferation using tritiated thymidine.

Figure 9:
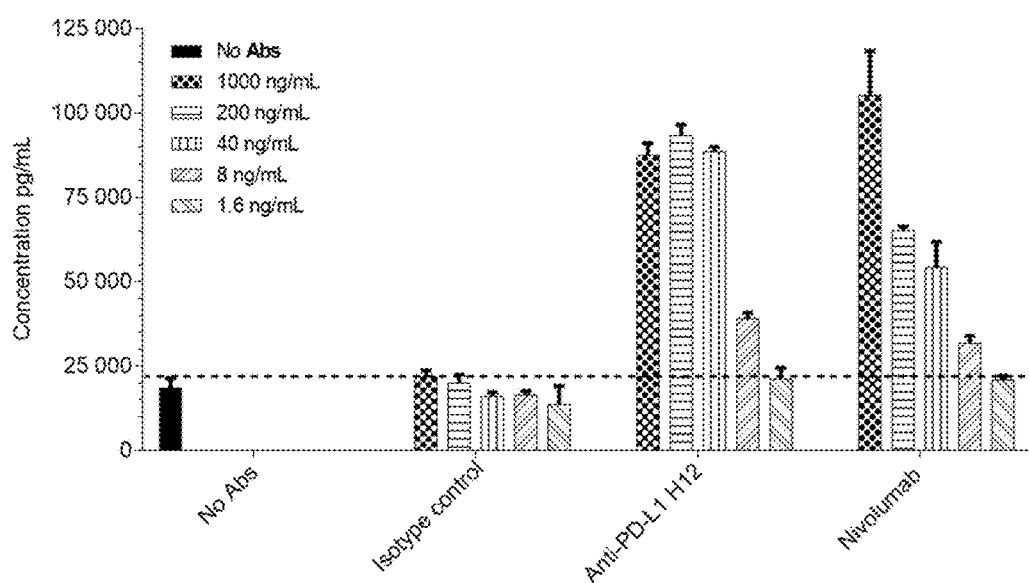
FIG. 9. Bar Chart showing IFNγ secretion of exhausted T cells in response to antibodies H12, nivolumab (commercial anti-PD-1 antibody), and isotype and no antibody control.
Figure 10:
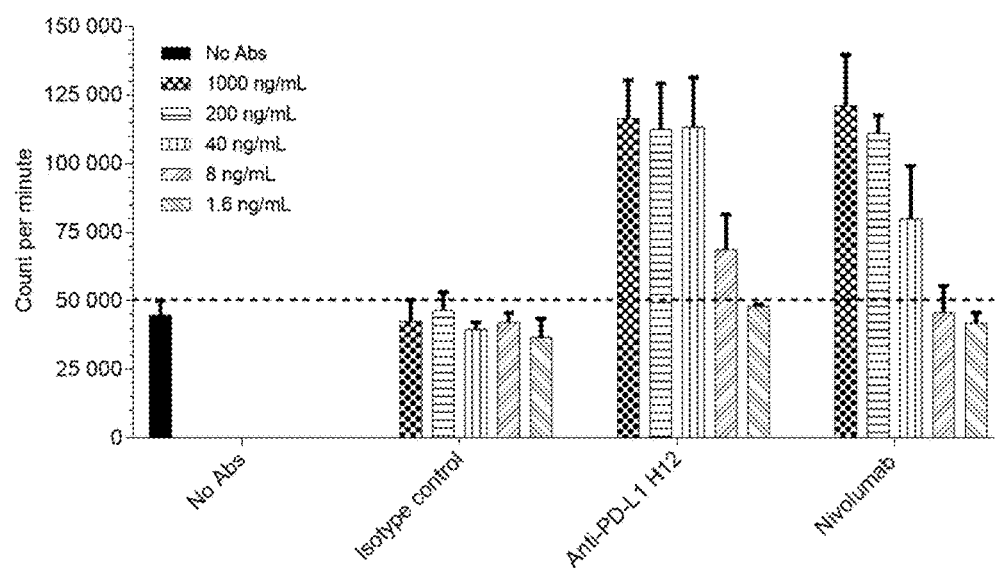
FIG. 10. Bar Chart showing proliferation of exhausted T cells in response to antibodies anti-PD-L1 H12, nivolumab, and isotype and no antibody control.

The results are shown in FIGS. 9 and 10. Antibody H12 was found to suppress T cell exhaustion, restoring both secretion of IFN-γ (FIG. 9) and proliferation (FIG. 10) of T cells. Proliferation and IFN-γ secretion were restored to a similar level by treatment with H12 at 1000 ng/ml as with treatment with Nivolumab at 1000 ng/ml. Notably, proliferation and IFN-γ secretion was higher for T cells treated with H12 antibody than Nivolumab at 200 ng/ml and 40 ng/ml concentrations.

Example 5: Antibody Affinity for PD-L1

Affinity for antibody H12 for human PD-L1 and murine PD-L1 was investigated by Surface Plasmon Resonance (SPR) analysis. Briefly, human or mouse PD-L1 coupled to Fc was immobilised on a sensor chip compatible with the Proteon XPR36 Bioanalyser (BioRad). Crude H12 Fab extract was then flown onto the chip and the association/dissociation was recorded and analysed and the affinity ($K_D$) was calculated.

Figure 11:
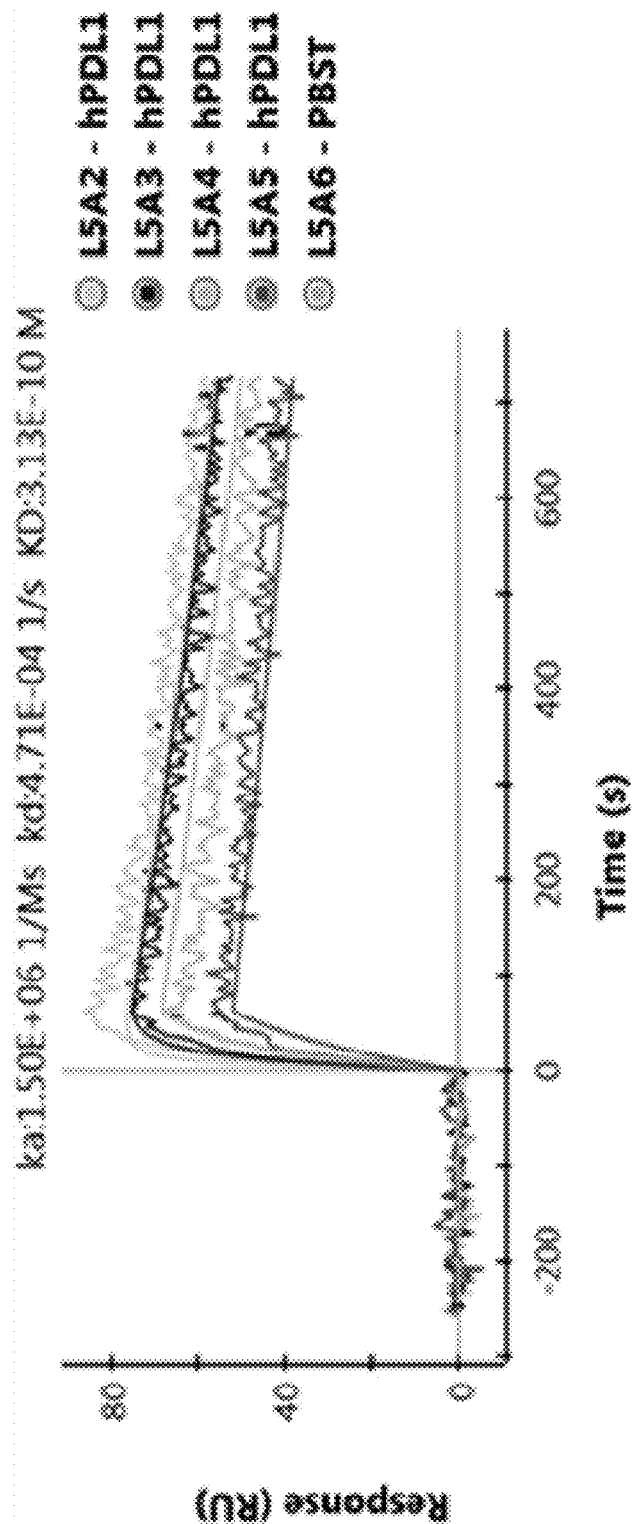
FIG. 11. Sensorgram showing affinity of anti-PD-L1 H12 for human PD-L1 as determined by surface plasmon resonance (SPR). KD=3.13×10$^{-10}$ M.
Figure 12:
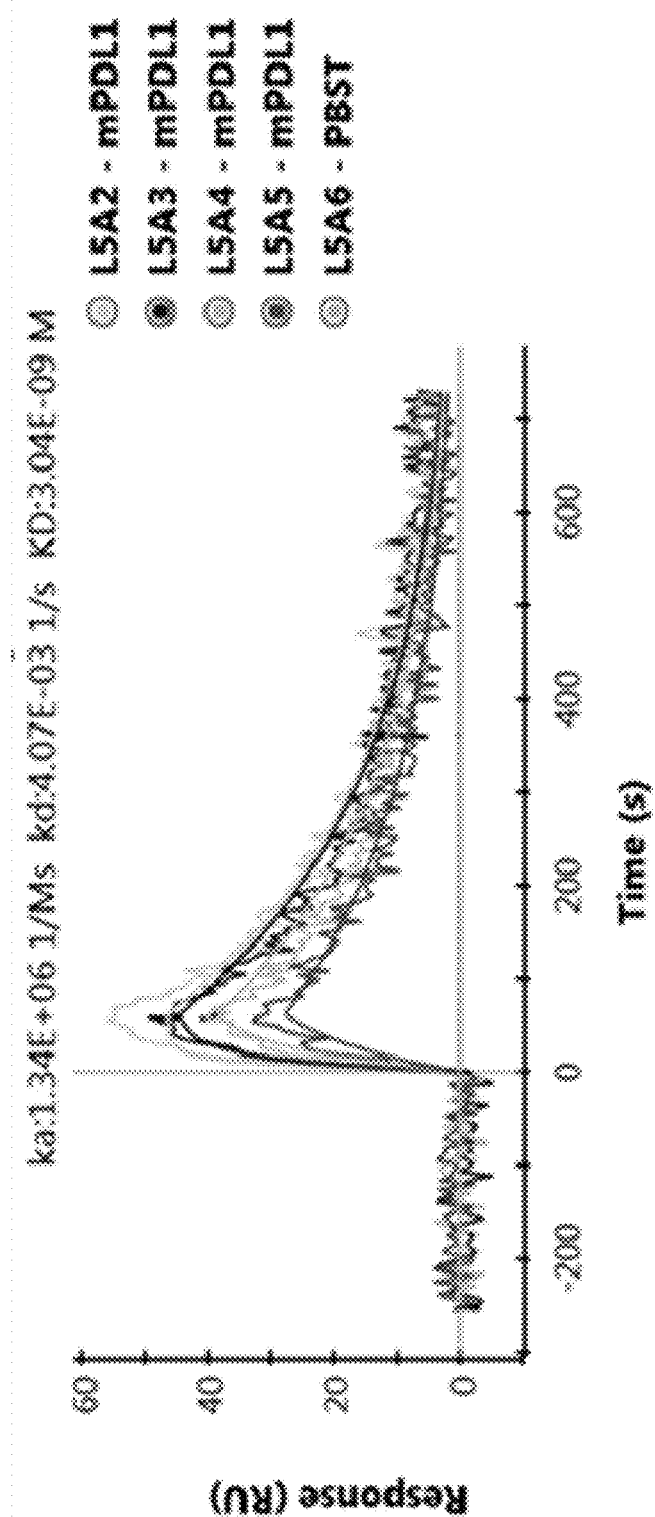
FIG. 12. Sensorgram showing affinity of anti-PD-L1 H12 for murine PD-L1 as determined by surface plasmon resonance (SPR). KD=3.04×10$^{-9}$ M.

The results are shown in FIGS. 11 and 12. H12 was found to have a high affinity for human PD-L1 of $K_D$=0.313 nM, and for murine PD-L1 of $K_D$=3.04 nM.

Example 6: Use of Anti-PD-L1 Antibodies to Treat Tumours: Ex Vivo Activation of Tumor Infiltrating Lymphocytes Lung tumour samples were obtained from the National Cancer Centre Singapore after approval. Samples were dissociated using a human tumour dissociation kit and a tissue dissociator device.

Figure 13A:
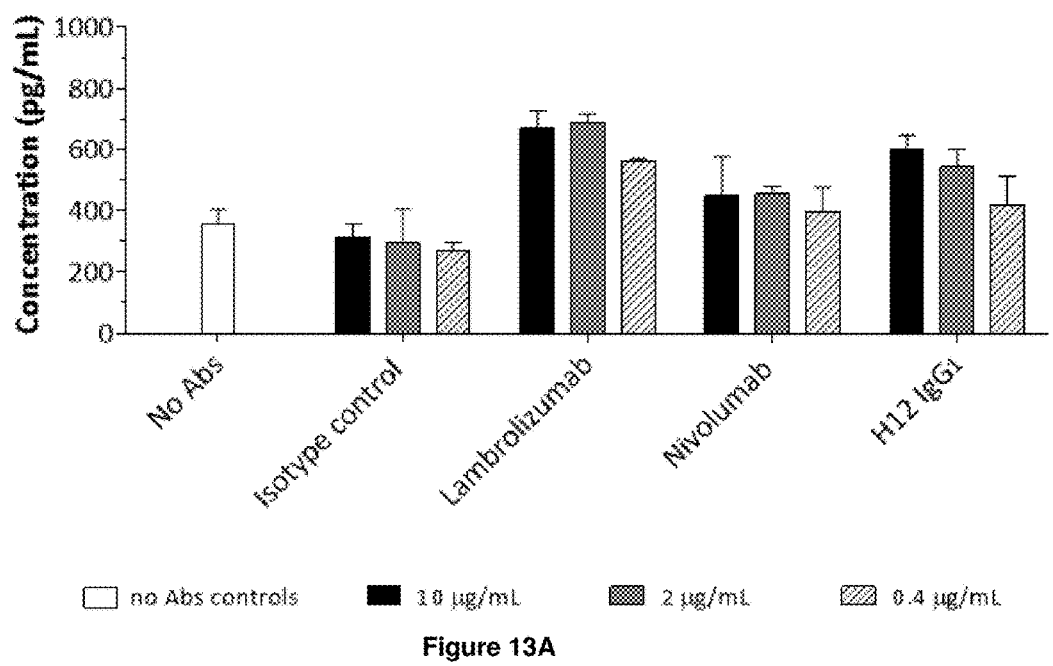
FIGS. 13A-B. Bar Charts showing IFNγ secretion (FIG. 13A) of dissociated lung tumor tissue and (FIG. 13B) dissociated lung tumor tissue co-cultured with allogenic dendritic cells (DC) in a mixed lymphocyte reaction (MLR), in response to nivolumab, labrolizumab (both commercial anti-PD-1 antibodies), antibody H12, and isotype and no antibody controls.

The tumour dissociated mixture was cultured with anti-PDL-1 IgG$_1$ clone H12 for 7 days prior to measurement of IFN-γ in the supernatant by ELISA. Nivolumab and lambrolizumab were used as positive controls in the assay (both are anti-PD-1 antibodies), an isotype antibody was used as a negative control. FIG. 13A shows secretion of IFN-γ by tumour infiltrating lymphocytes after 7 days of culture in the presence of the antibodies. H12 re-activated lymphocytes to secrete IFN-γ in a dose-dependent manner.

Another fraction of the dissociated mixture was co-cultured with allogeneic dendritic cells (DC) to initiate a mixed lymphocyte reaction (MLR). Cells were first cultured for 7 days without antibodies and then for 7 days in the presence of H12 or control antibodies. After these 2 rounds, IFN-γ was assayed in supernatants by ELISA.

Figure 13B:
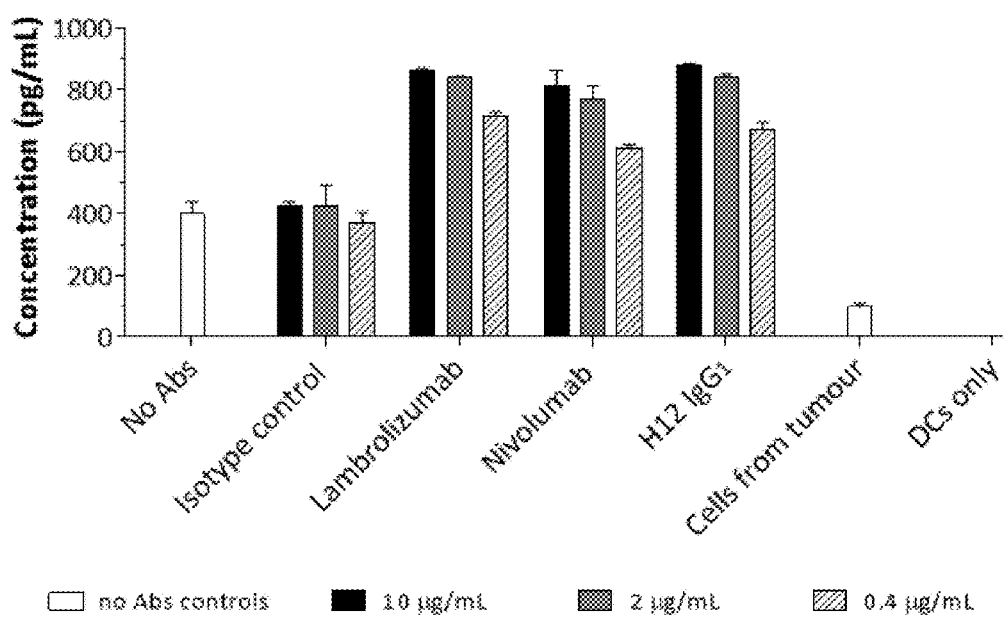

FIG. 13B shows secretion of IFN-γ after the MLR in the presence of the antibodies. H12 restored the ability of tumour lymphocytes to secrete IFN-γ in a dose-dependent manner.

Example 7: Use of Anti-PD-L1 Antibodies to Treat Infections: Autologous Activation of T Cells in the Presence of Influenza Blood was collected from Influenza-positive donors. Monocyte-derived DCs were infected with influenza virus A/PR/8/34 (H1N1). Infected DCs were mixed to PBMCs from the same donor for a first round of culture of 5 days. Cells were then cultured for a second round of 5 days in the presence of H12 or control antibodies. After these 2 rounds, most of the cells in culture are Influenza-specific T cells. At the end of 2 rounds of culture, IFN-γ was assayed in supernatants by ELISA. In this assay, H12 was tested either as an $IgG_1$ antibody or as an $IgG_4$ antibody.

Figure 14:
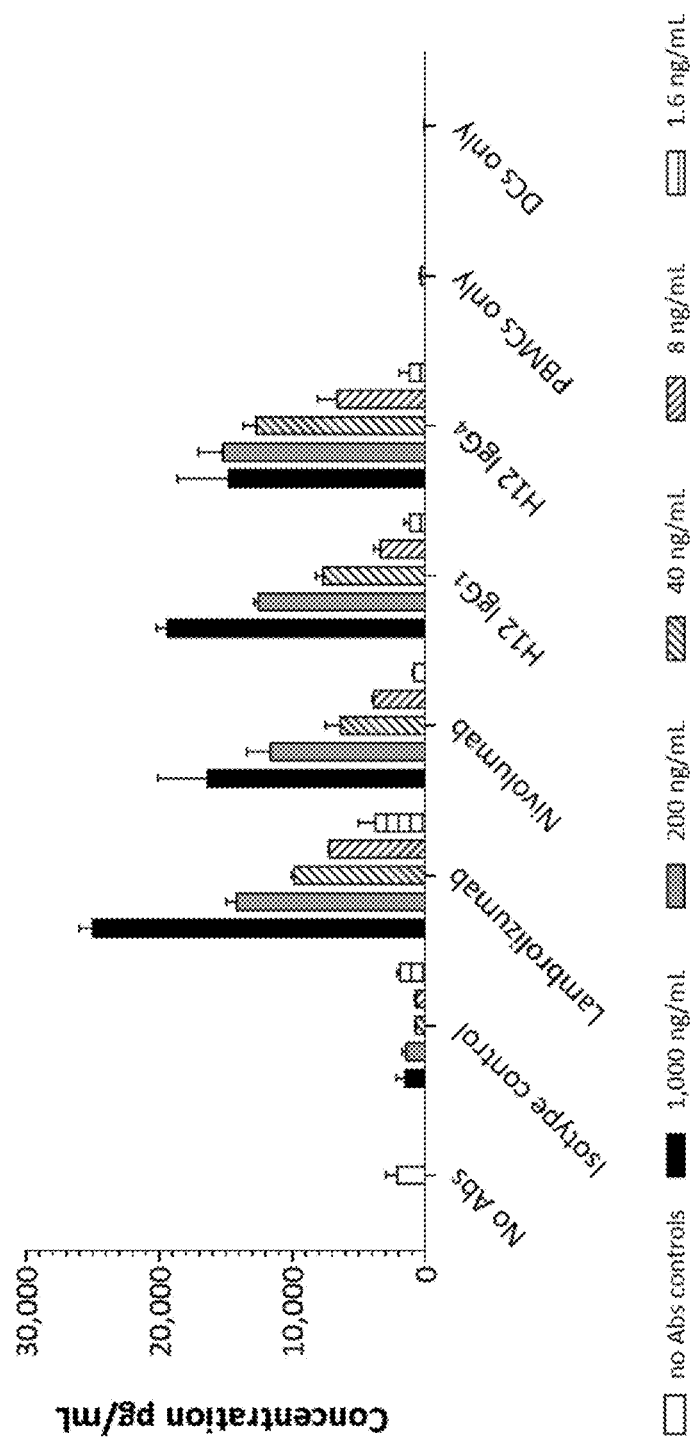
FIG. 14. Bar Chart showing IFNγ secretion after culture of PBMCs with Influenza in the presence of the nivolumab, labrolizumab, antibody H12-IgG$_4$, antibody H12-IgG$_1$, and isotype and no antibody controls.

FIG. 14 shows secreted IFN-γ after culture of PBMCs with Influenza in the presence of the antibodies. Both $H12-IgG_1$ and $H12-IgG_4$ were able to restore the capacity of lymphocytes to secrete IFN-γ upon viral stimulation in a dose-dependent manner.

Example 8: Specificity/Cross-Reactivity of H12

Recognition of various members of the CD28 family by H12 was tested by ELISA.

Figure 15:
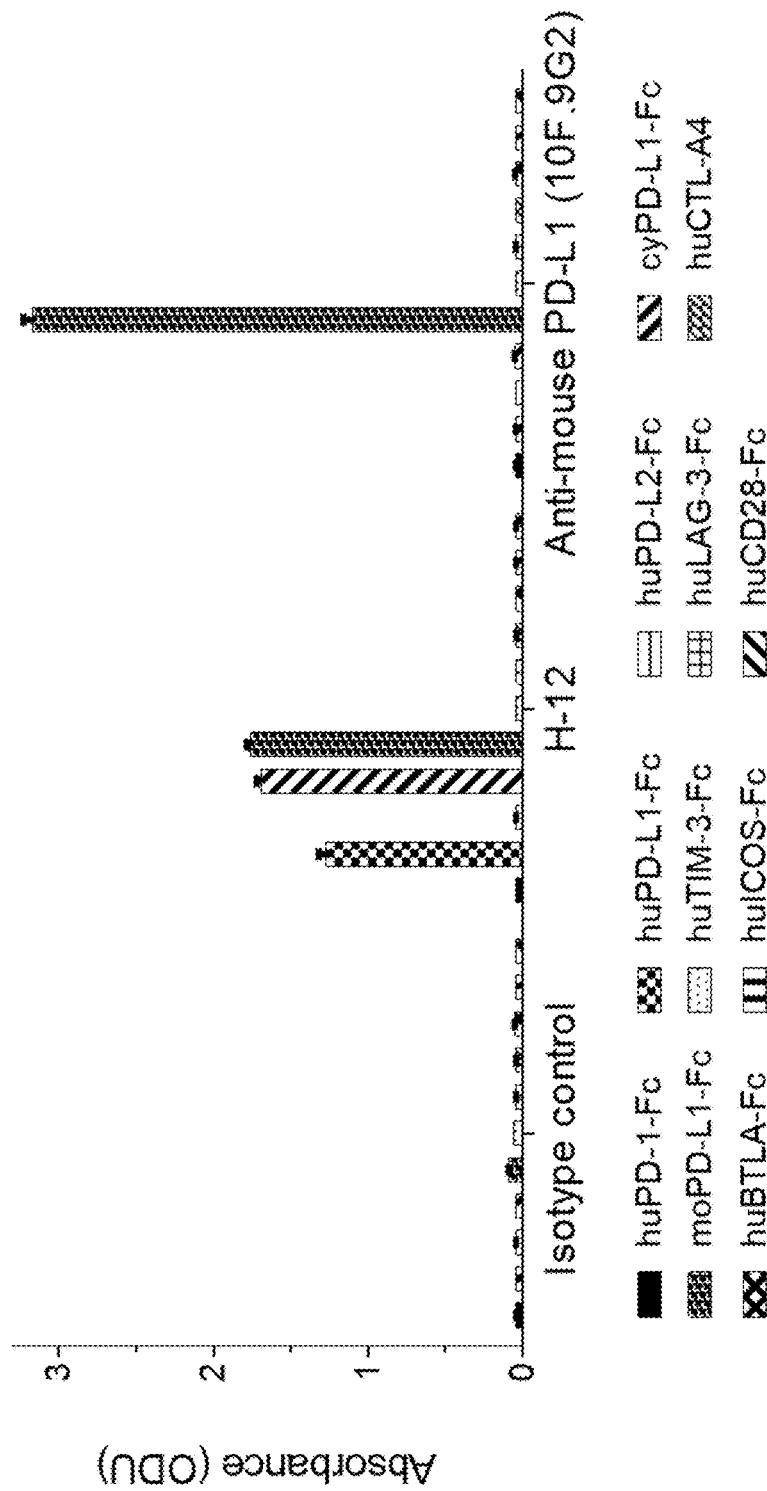
FIG. 15. Bar Chart showing ELISA with H12 on different antigens: human (hu) PD-1, PD-L1, PD-L2, TIM-3, LAG-3, CTL-A4, BLTA, ICOS and CD28, and cynomolgus (cy) and mouse (mo) PD-L1.

FIG. 15 shows the ELISA with H12 on different antigens: human (hu) PD-1, PD-L1, PD-L2, TIM-3, LAG-3, CTL-A4, BLTA, ICOS and CD28, and cynomolgus (cy) and mouse (mo) PD-L1. H12 displayed specificity for the PD-L1 molecule, and cross-reactivity among species.

Example 9: Preliminary In Vivo Efficacy of H12 Antibody

H12 was tested in 2 tumour models: a colon cancer model using CT26 cell line and a melanoma model using B16F10 cell line.

Balb/C or C57BL/6 mice were inoculated in the left flank with $0.5×10^6$ CT26 or $0.2×10^6$ B16F10 tumour cells, respectively, at day 0, and injected intraperitoneally with 250 μg of H12 or isotype IgG1 at days 7, 11, 14, 18 and 21. Tumour growth was then analysed, size was measured with a caliper and volume calculated as follows: $V=l^2×L/2$ (with l=shorter side and L=longer side).

Figure 16A:
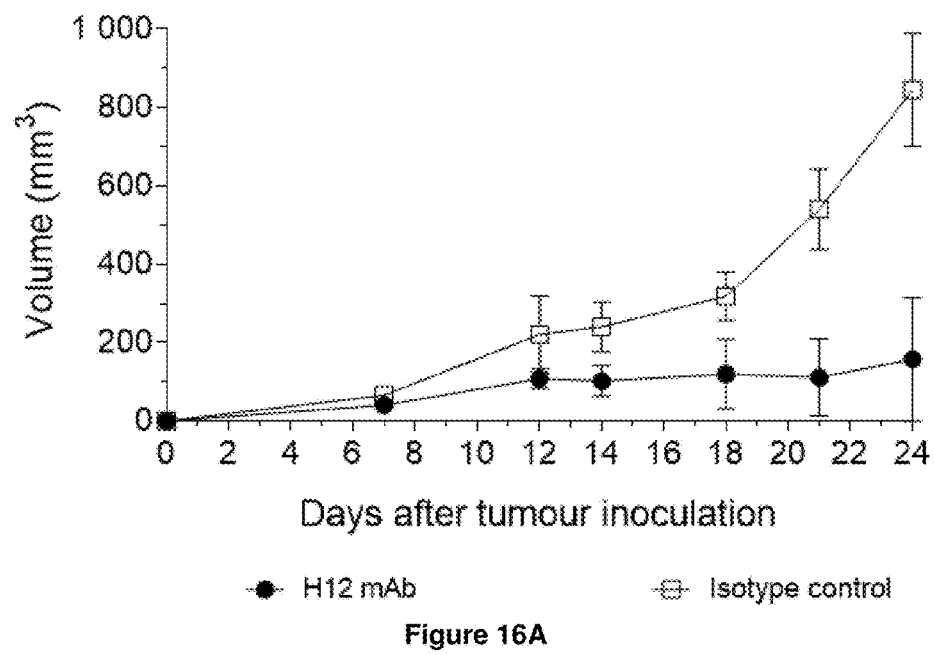
FIGS. 16A-B. Graphs showing inhibition of tumour growth by antibody H12 in (FIG. 16A) a mouse colon cancer model using CT26 cell line and (FIG. 16B) a mouse melanoma model using B16F10 cell line.
Figure 16B:
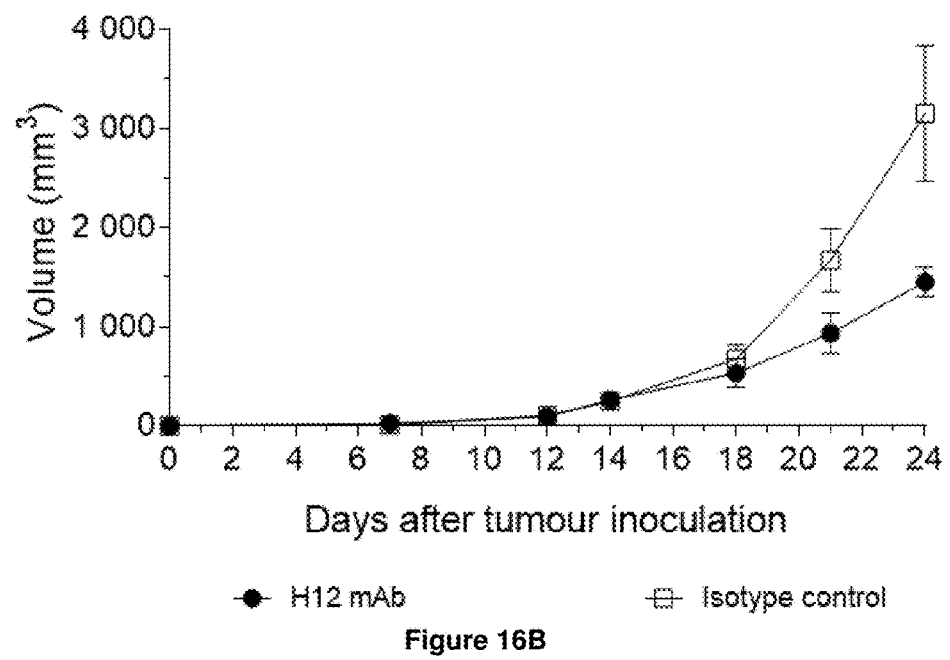

FIGS. 16A and 16B show tumour growth after tumour inoculation in both models. H12 inhibited tumour growth in both models.

Example 10: Data with Engineered H12 Antibody

H12 clone was engineered in order to revert its framework to a germline-like framework; the heavy chain of the new clone H12_GL was slightly modified, the light chain remained the same as for H12 original clone.

H12_GL was tested in a blocking assay. Briefly HEK 293 cells were transfected with the pcDNA3.1 plasmid expressing human PD-L1 protein using 293tfectin (Invitrogen), according to manufacturer's protocol. PD-L1 expression was confirmed with commercial anti-mouse or anti-human PD-L1 conjugated to PECy7 (Biolegend). 50 to 100 nM of recombinant human PD-1 labelled with Phycoerythrin (PE) was used to bind the PD-L1 expressed on the transfected cells. Serially diluted antibodies (anti-PD-L1 H12, H12_GL or isotype control) were mixed with the human PD-1-PE for 30 minutes before being added to the PD-L1 transfected cells. Cells were washed 3 times with PBS and all data were collected on a BD FACSCanto II (BD Bioscience) and analysed on BD FACSDiva software (BD Bioscience).

Figure 17:
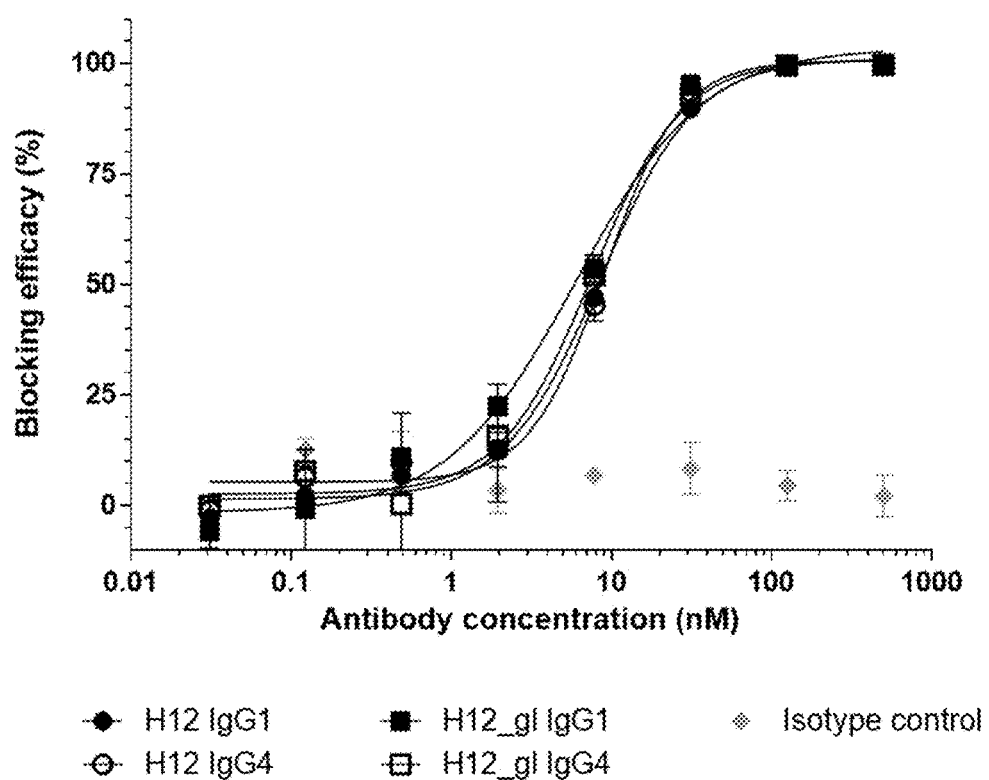
FIG. 17. Graph showing efficiency of blocking of interaction between PD-1 and PD-L1 by antibodies H12-IgG$_1$, H12-IgG$_4$, H12_GL-IgG$_1$, and H12_GL-IgG$_4$, as determined by blocking assay using HEK293-6E cells transfected with human PD-L1.

FIG. 17 shows that H12_GL blocked PD-1/PD-L1 interactions as efficiently as H12.

Example 11: In Vivo Efficacy of Anti-PD-L1 Antibody H12: Control of Tumour Growth in Mouse Model Because H12 was shown to cross-react with mouse PD-L1, this antibody was evaluated for ability to control tumour growth in a mouse model using colon carcinoma MC38 cells.

Two million MC38 cells were inoculated to mice subcutaneously at day 0, and five doses of 200 μg per animal of the anti-PD-L1 H12 $IgG_1$ or isotype control antibody were injected intraperitoneally, starting at day 8. Tumour size was measured throughout the experiment.

Figure 18A:
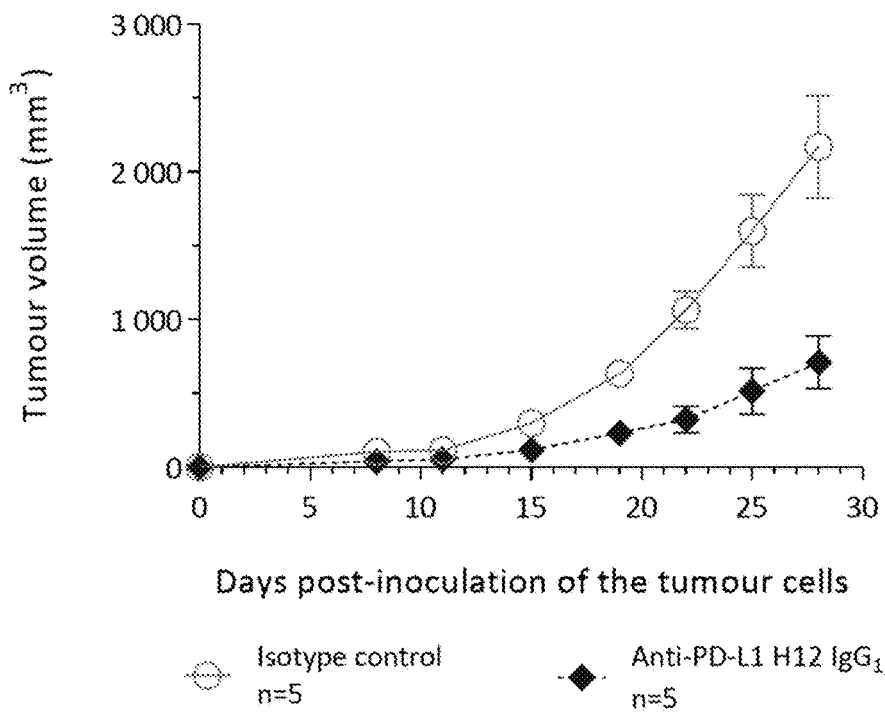
FIGS. 18A-B. Graphs showing in vivo efficiency of anti-PD-L1 antibody H12 to control tumour growth in a mouse model. MC38 cells were inoculated into mice, and five doses of 200 μg per animal of the indicated antibody were given intraperitoneally starting at day 8.
Figure 18B:
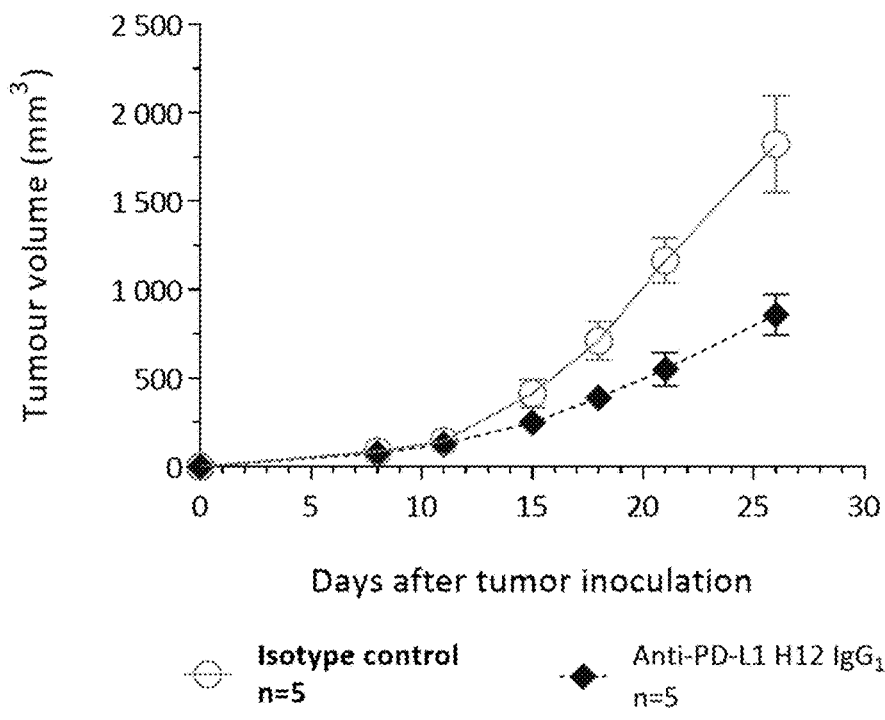

The results for two independent experiments are shown in FIGS. 18A and 18B. The graphs show tumour growth (mean±SEM) in the MC38 tumour growth model in the presence of anti-PD-L1 antibody H12 or negative isotype control. In both experiments, H12 was able to control tumour growth.

Example 12: Binding of Anti-PD-L1 mAbs to the Target and Comparison with Atezolizumab Binding of anti-PD-L1 clones H12 and C4 to human PD-L1 was compared to that of atezolizumab, a commercially available anti-PD-L1 IgG1 antibody.

Antibodies were coated to a plate and various concentrations of biotinylated PD-L1 were added. Binding was measured by ELISA. Antibodies were coated onto maxisorp plates at 2 15 μg/mL in coating buffer and incubated overnight at 4° C. The next day, plates were washed with wash buffer (PBS+0.05% Tween-20), and blocker with casein for 1 hour, at room temperature. Plates were then washed again using wash buffer. Various concentrations of biotinylated human PD-L1 were then added to the plates, and the plates were then incubated at room temperature for 1 hour. Plates were then washed again using wash buffer. Streptavidin-HRP was then added and incubated for 1 hour at room temperature to detect biotinylated human PD-L1 bound to the different antibodies. Plates were then washed again using wash buffer. Finally, TMB was added to develop the ELISA; TMB conversion by HRP was stopped using 1M H—Cl.

Avidity was also assessed by ELISA, with PD-L1 antigen bound onto a plate at single concentration, and addition of various concentrations of antibodies. A secondary antibody was used to detect anti-PD-L1 antibody complexed to the antigen. Neutravidin was coated onto maxisorp plates at 2 μg/mL in coating buffer and incubated overnight at 4° C. The next day, plates were washed with wash buffer (PBS+0.05% Tween-20), and blocker with casein for 1 hour, at room temperature. Plates were then washed again using wash buffer. Biotinylated human PD-L1 was then added to the plates at 0.2 μg/mL and incubated for 1 hour at room temperature. Plates were then washed again using wash buffer. The different antibodies were then added at various concentrations, and incubated for 1 hour at room temperature. Plates were then washed again using wash buffer. Anti-human Fc-HRP was then added and incubated for 1 hour at room temperature. Plates were then washed again using wash buffer. Finally, TMB was added to develop the ELISA; TMB conversion by HRP was stopped using 1M H—Cl.

Figure 19A:
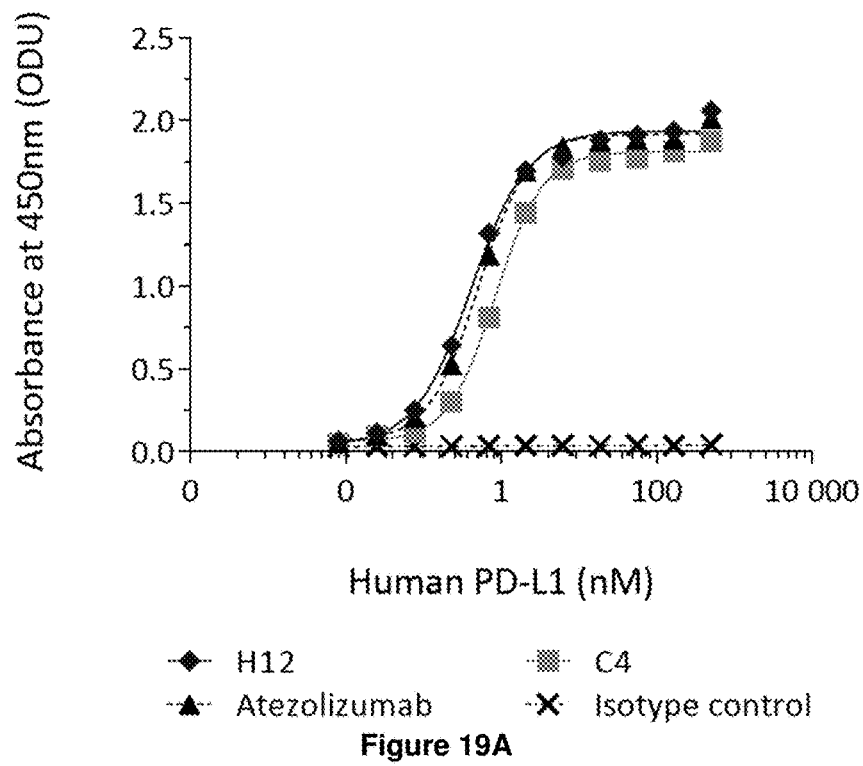
FIGS. 19A-B. Graphs showing binding of antibodies H12, C4 and atezolizumab to human PD-L1, and avidity of binding.

FIG. 19A presents the binding of the antibodies (and isotype control) to PD-L1 (mean±SD of duplicates). H12 shows a similar binding curve for PD-L1 as atezolizumab. Affinity of H12 for PD-L1 is higher than affinity of atezolizumab for PD-L1.

Figure 19B:
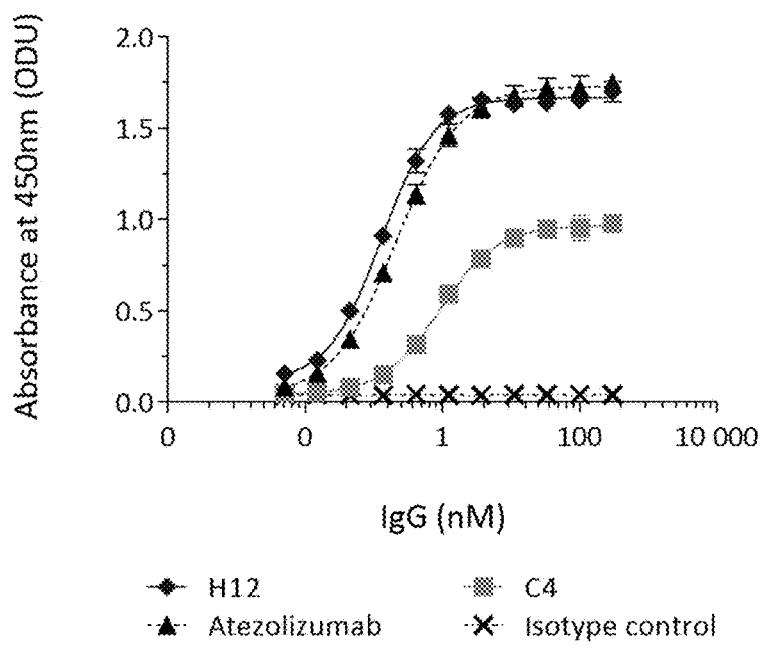

FIG. 19B presents the avidity of the antibodies for their target (mean±SD of duplicates). H12 shows a high avidity to PD-L1, similar to atezolizumab, while C4 shows a medium avidity. Avidity of H12 for PD-L1 is higher than avidity of atezolizumab for PD-L1.

Binding to PD-L1 was also tested by investigating binding to a MDA-MB-231 human breast cancer cell line that constitutively expresses PD-L1 at the cell membrane. Binding of the antibodies was measured by flow cytometry.

Figure 20:
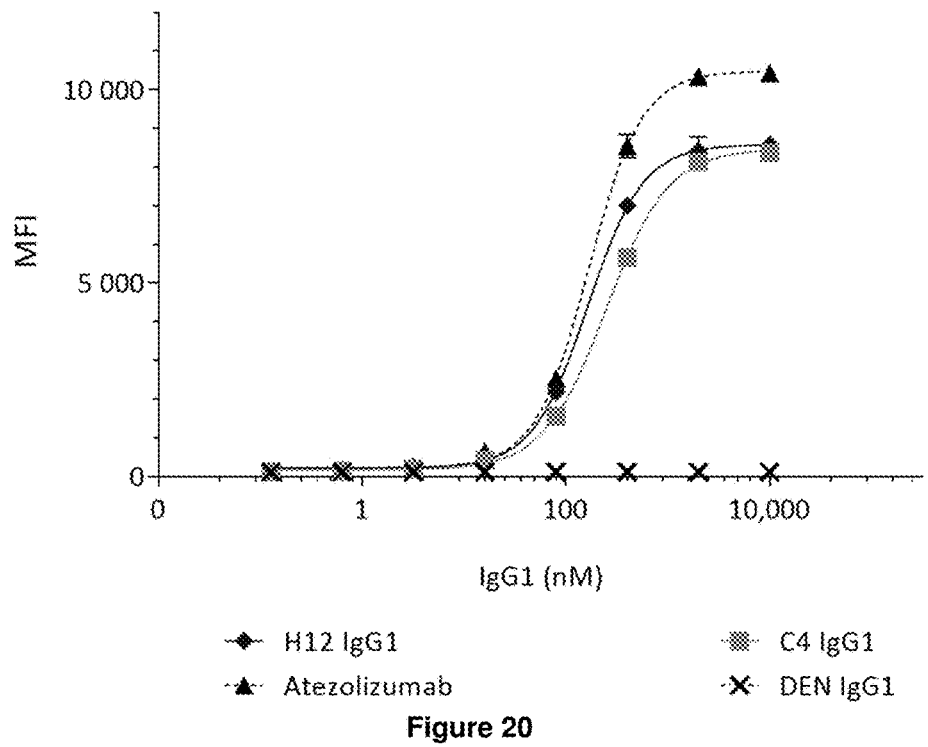
FIG. 20. Graph showing binding of H12 IgG1, C4 IgG1, atezolizumab and DEN IgG1 antibodies to MDA-MB-231 human breast cancer cells. Mean fluorescence index (MFI) is shown (mean±SD of duplicates).

FIG. 20 presents the mean fluorescence index (MFI) for different concentrations of antibodies (mean±SD of duplicates). The anti-PD-L1 antibodies H12 IgG1 and C4 IgG1 bind efficiently to cells expressing PD-L1.

Example 13: In Vitro Activity of Anti-PD-L1 Antibodies: Blocking of PD-L1 Binding to PD-1

The ability of the antibodies to block the binding of PD-L1 to its receptor PD-1 was assessed by ELISA. Briefly, the antibodies were pre-incubated with PD-L1 and then added onto ELISA plates onto which PD-1 was coated. After washing, the presence of PD-1-bound PD-L1 was detected with an antibody.

Figure 21:
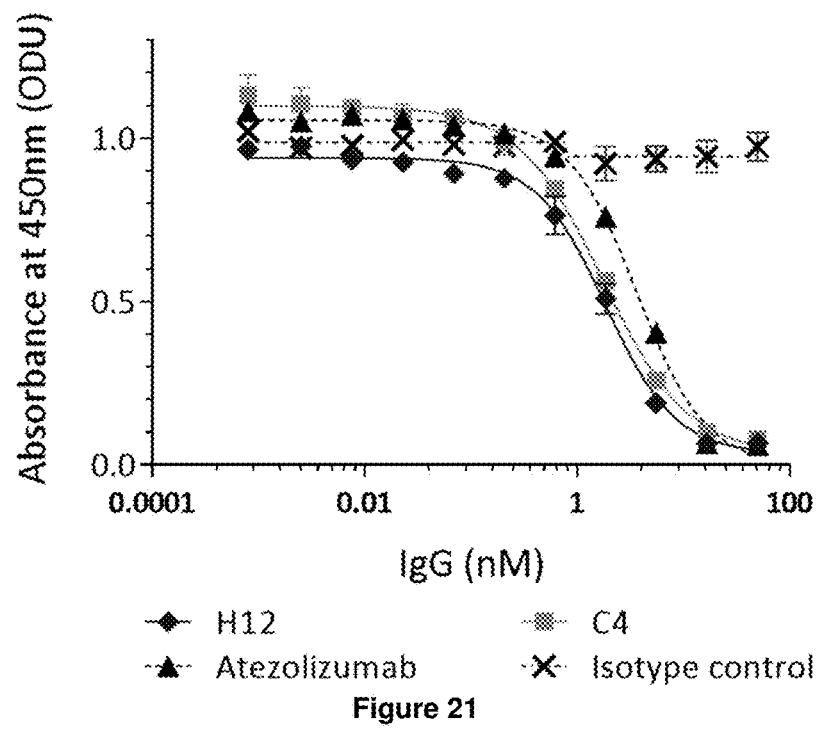
FIG. 21. Graph showing binding of PD-L1 to PD-1 in the presence of H12, C4, atezolizumab and isotype control antibodies. The graph shows ability of antibodies to block binding of PD-L1 to its receptor PD-1 (mean±SD of duplicates).

FIG. 21 presents the results of experiments investigating binding of PD-L1 to PD-1 in the presence or absence of anti-PD-L1 antibodies (or isotype control) (mean±SD of duplicates). The anti-PD-L1 antibodies H12 and C4 are able to block the binding to PD-L1 to its receptor PD-1. Both H12 and C4 were able to block interaction between PD-L1 and PD-1 with greater efficiency than atezolizumab.

The invention claimed is:

1. A method of treating cancer, comprising administering an antibody or antigen binding fragment to a patient suffering from a cancer, wherein the antibody or antigen binding fragment binds to PD-L1, and comprises:
at least one light chain variable region incorporating the following CDRs:
LC-CDR1: TGSSSNIGAGYDVH (SEQ ID NO:18)
LC-CDR2: GNSNRPS (SEQ ID NO:19)
LC-CDR3: QSYDSSLSGSYVV (SEQ ID NO:20); and
at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: SGHGYSYGAFDY (SEQ ID NO:25).

2. The method of claim 1, wherein the antibody or antigen binding fragment comprises a heavy chain variable region sequence having at least 85% sequence identity to the amino acid sequence of SEQ ID NO:8 or 35, and a light chain variable region sequence having at least 85% sequence identity to the amino acid sequence of SEQ ID NO:4.

3. The method of claim 1, wherein the antibody or antigen binding fragment comprises a heavy chain variable region comprising the amino acid sequence of SEQ ID NO:8 or 35, and a light chain variable region comprising the amino acid sequence of SEQ ID NO:4.

4. The method of claim 1, wherein the cancer is a cancer of a tissue selected from the group consisting of lung, colon, skin, breast, liver, stomach, nasopharynx, oral cavity, oesophagus, larynx, salivary gland, tongue, tonsil, trachea, kidney, bladder, and blood.

5. The method of claim 1, wherein the cancer is selected from the group consisting of lung cancer, non-small cell lung cancer (NSCLC), colon cancer, colon carcinoma, colorectal carcinoma, skin cancer, melanoma, metastatic melanoma, breast cancer, liver cancer, hepatoma, stomach cancer, head and neck cancer, nasopharyngeal cancer, oral cavity cancer, oesophageal cancer, laryngeal cancer, salivary gland cancer, tongue cancer, tonsil cancer, tracheal cancer, renal cancer, bladder cancer, haematologic cancer, lymphoma and Hodgkin's lymphoma.

6. The method of claim 1, wherein the administration of the antibody or antigen binding fragment is intravenous.

7. The method of claim 1, wherein the antibody comprises a human constant region selected from IgG1, IgG2, IgG3 and IgG4.

8. The method of claim 1, wherein the antigen binding fragment is a Fab fragment or scFv fragment.

9. A method of treating cancer, comprising administering an antibody or antigen binding fragment to a patient suffering from a cancer, wherein the antibody or antigen binding fragment binds to PD-L1, and comprises:
a heavy chain variable region comprising the amino acid sequence of SEQ ID NO:8 or 35, and
the light chain variable region comprising the amino acid sequence of SEQ ID NO:4.

10. The method of claim 9, wherein the cancer is a cancer of a tissue selected from the group consisting of lung, colon, skin, breast, liver, stomach, nasopharynx, oral cavity, oesophagus, larynx, salivary gland, tongue, tonsil, trachea, kidney, bladder, and blood.

11. The method of claim 9, wherein the cancer is selected from the group consisting of lung cancer, non-small cell lung cancer (NSCLC), colon cancer, colon carcinoma, colorectal carcinoma, skin cancer, melanoma, metastatic melanoma, breast cancer, liver cancer, hepatoma, stomach cancer, head and neck cancer, nasopharyngeal cancer, oral cavity cancer, oesophageal cancer, laryngeal cancer, salivary gland cancer, tongue cancer, tonsil cancer, tracheal cancer, renal cancer, bladder cancer, haematologic cancer, lymphoma and Hodgkin's lymphoma.

12. The method of claim 9, wherein the administration of the antibody or antigen binding fragment is intravenous.

13. The method of claim 9, wherein the antibody comprises a human constant region selected from IgG1, IgG2, IgG3 and IgG4.

14. The method of claim 9, wherein the antigen binding fragment is a Fab fragment or scFv fragment.

15. A method of treating cancer in a subject, comprising:
culturing T cells obtained from a blood sample from a subject having a cancer in the presence of an antibody or antigen binding fragment which binds to PD-L1 to expand a T cell population; and
administering the expanded T cell population to the subject;
wherein the antibody or antigen binding fragment which binds to PD-L1 comprises: at least one light chain variable region incorporating the following CDRs:
LC-CDR1: TGSSSNIGAGYDVH (SEQ ID NO:18)
LC-CDR2: GNSNRPS (SEQ ID NO:19)
LC-CDR3: QSYDSSLSGSYVV (SEQ ID NO:20); and
at least one heavy chain variable region incorporating the following CDRs:
HC-CDR1: SYAIS (SEQ ID NO:21)
HC-CDR2: RIIPILGIANYAQKFQG (SEQ ID NO:22)
HC-CDR3: SGHGYSYGAFDY (SEQ ID NO:25).

16. The method of claim 15, wherein the antibody or antigen binding fragment comprises a heavy chain variable region comprising the amino acid sequence of SEQ ID NO:8 or 35, and a light chain variable region comprising the amino acid sequence of SEQ ID NO:4.

17. The method of claim 15, wherein the cancer is a cancer of a tissue selected from the group consisting of lung, colon, skin, breast, liver, stomach, nasopharynx, oral cavity, oesophagus, larynx, salivary gland, tongue, tonsil, trachea, kidney, bladder, and blood.

18. The method of claim 15, wherein the cancer is selected from the group consisting of lung cancer, non-small cell lung cancer (NSCLC), colon cancer, colon carcinoma, colorectal carcinoma, skin cancer, melanoma, metastatic melanoma, breast cancer, liver cancer, hepatoma, stomach cancer, head and neck cancer, nasopharyngeal cancer, oral cavity cancer, oesophageal cancer, laryngeal cancer, salivary gland cancer, tongue cancer, tonsil cancer, tracheal cancer, renal cancer, bladder cancer, haematologic cancer, lymphoma and Hodgkin's lymphoma.

19. The method of claim 15, wherein the antibody comprises a human constant region selected from IgG1, IgG2, IgG3 and IgG4.

20. The method of claim 15, wherein the antigen binding fragment is a Fab fragment or scFv fragment.

\* \* \* \* \*

```
SEQUENCE LISTING

<160> NUMBER OF SEQ ID NOS: 36

<210> SEQ ID NO 1
<211> LENGTH: 110
<212> TYPE: PRT
<213> ORGANISM: Homo sapiens

<400> SEQUENCE: 1

Gln Ser Val Leu Thr Gln Pro Pro Ser Val Ser Ala Ala Pro Gly Gln
1               5                   10                  15

Arg Val Ser Ile Ser Cys Ser Gly Arg Ser Ser Asn Ile Ala Ser His
            20                  25                  30

Asp Val Phe Trp Tyr Gln Gln Leu Pro Gly Thr Ala Pro Lys Ile Val
        35                  40                  45

Met Tyr Glu Thr Asn Lys Arg Pro Trp Gly Ile Pro Asp Arg Phe Ser
    50                  55                  60

Gly Ser Lys Ser Gly Thr Ser Ala Thr Leu Asp Ile Ala Gly Leu Gln
65                  70                  75                  80

Thr Gly Asp Glu Ala Asp Tyr Tyr Cys Gly Ala Trp Asp Ser Gly Leu
                85                  90                  95

Thr Gly Met Leu Phe Gly Gly Gly Thr Lys Val Thr Val Leu
            100                 105                 110

<210> SEQ ID NO 2
<211> LENGTH: 105
<212> TYPE: PRT
<213> ORGANISM: Homo sapiens

<400> SEQUENCE: 2

Ser Tyr Glu Leu Thr Gln Pro Pro Ser Val Ser Val Ala Pro Gly Lys
1               5                   10                  15

Thr Thr Arg Ile Thr Cys Gly Gly Asp Asn Ile Gly Arg Lys Ser Val
            20                  25                  30

His Trp Tyr Gln Gln Arg Pro Gly Gln Ala Pro Leu Leu Leu Val Tyr
        35                  40                  45

Asp Asp Gly Asp Arg Pro Ser Gly Ile Pro Asp Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Thr Val Val Phe
                85                  90                  95

Gly Gly Gly Thr Arg Leu Thr Val Leu
```

100                 105

<210> SEQ ID NO 3
<211> LENGTH: 110
<212> TYPE: PRT
<213> ORGANISM: Homo sapiens

<400> SEQUENCE: 3

Gln Ser Val Val Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Glu Arg Leu Ser Gly Ile Pro Asp Arg Phe Ser
    50                  55                  60

Gly Ser Lys Ser Gly Thr Ser Ala Thr Leu Gly Ile Ser Gly Leu Gln
65                  70                  75                  80

Thr Gly Asp Glu Ala Asp Tyr Tyr Cys Gly Thr Trp Asp Ser Ser Leu
                85                  90                  95

Ser Val Val Val Phe Gly Gly Gly Thr Lys Leu Thr Val Leu
            100                 105                 110

<210> SEQ ID NO 4
<211> LENGTH: 113
<212> TYPE: PRT
<213> ORGANISM: Homo sapiens

<400> SEQUENCE: 4

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Tyr Val Val Phe Gly Gly Gly Thr Lys Leu Thr Val
            100                 105                 110

Leu

<210> SEQ ID NO 5
<211> LENGTH: 121
<212> TYPE: PRT
<213> ORGANISM: Homo sapiens

<400> SEQUENCE: 5

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Tyr Gly Ser Leu Tyr Ala Phe Asp Ile Trp Gly
                100                 105                 110

Gln Gly Thr Met Val Thr Val Ser Ser
            115                 120
```

<210> SEQ ID NO 6
<211> LENGTH: 121
<212> TYPE: PRT
<213> ORGANISM: Homo sapiens

<400> SEQUENCE: 6

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Ser Tyr Gly Ser Leu Tyr Ala Phe Asp Ile Trp Gly
                100                 105                 110

Gln Gly Thr Thr Val Thr Val Ser Ser
            115                 120
```

<210> SEQ ID NO 7
<211> LENGTH: 122
<212> TYPE: PRT
<213> ORGANISM: Homo sapiens

<400> SEQUENCE: 7

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Gly Asn Ser Leu Tyr Ala Phe Asp Ile Trp
                100                 105                 110

Gly Gln Gly Thr Met Val Thr Val Ser Ser
            115                 120
```

<210> SEQ ID NO 8
<211> LENGTH: 116
<212> TYPE: PRT
<213> ORGANISM: Homo sapiens

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly His Gly Tyr Ser Tyr Gly Ala Phe Asp Tyr Trp Gly
            100                 105                 110

Gln Gly Thr Leu
        115

<210> SEQ ID NO 9
<211> LENGTH: 13
<212> TYPE: PRT
<213> ORGANISM: Homo sapiens

<400> SEQUENCE: 9

Ser Gly Arg Ser Ser Asn Ile Ala Ser His Asp Val Phe
1               5                   10

<210> SEQ ID NO 10
<211> LENGTH: 7
<212> TYPE: PRT
<213> ORGANISM: Homo sapiens

<400> SEQUENCE: 10

Glu Thr Asn Lys Arg Pro Trp
1               5

<210> SEQ ID NO 11
<211> LENGTH: 11
<212> TYPE: PRT
<213> ORGANISM: Homo sapiens

<400> SEQUENCE: 11

Gly Ala Trp Asp Ser Gly Leu Thr Gly Met Leu
1               5                   10

<210> SEQ ID NO 12
<211> LENGTH: 11
<212> TYPE: PRT
<213> ORGANISM: Homo sapiens

<400> SEQUENCE: 12

Gly Gly Asp Asn Ile Gly Arg Lys Ser Val His
1               5                   10

<210> SEQ ID NO 13
<211> LENGTH: 7

<212> TYPE: PRT
<213> ORGANISM: Homo sapiens

<400> SEQUENCE: 13

Asp Asp Gly Asp Arg Pro Ser
1               5

<210> SEQ ID NO 14
<211> LENGTH: 8
<212> TYPE: PRT
<213> ORGANISM: Homo sapiens

<400> SEQUENCE: 14

Gln Ala Trp Asp Ser Thr Val Val
1               5

<210> SEQ ID NO 15
<211> LENGTH: 13
<212> TYPE: PRT
<213> ORGANISM: Homo sapiens

<400> SEQUENCE: 15

Ser Gly Ser Ser Ser Asn Ile Gly Asn Asn Tyr Val Ser
1               5                   10

<210> SEQ ID NO 16
<211> LENGTH: 7
<212> TYPE: PRT
<213> ORGANISM: Homo sapiens

<400> SEQUENCE: 16

Asp Asn Asn Glu Arg Leu Ser
1               5

<210> SEQ ID NO 17
<211> LENGTH: 11
<212> TYPE: PRT
<213> ORGANISM: Homo sapiens

<400> SEQUENCE: 17

Gly Thr Trp Asp Ser Ser Leu Ser Val Val Val
1               5                   10

<210> SEQ ID NO 18
<211> LENGTH: 14
<212> TYPE: PRT
<213> ORGANISM: Homo sapiens

<400> SEQUENCE: 18

Thr Gly Ser Ser Ser Asn Ile Gly Ala Gly Tyr Asp Val His
1               5                   10

<210> SEQ ID NO 19
<211> LENGTH: 7
<212> TYPE: PRT
<213> ORGANISM: Homo sapiens

<400> SEQUENCE: 19

Gly Asn Ser Asn Arg Pro Ser
1               5

<210> SEQ ID NO 20
<211> LENGTH: 13
<212> TYPE: PRT
<213> ORGANISM: Homo sapiens

```
<400> SEQUENCE: 20

Gln Ser Tyr Asp Ser Ser Leu Ser Gly Ser Tyr Val Val
1               5                   10

<210> SEQ ID NO 21
<211> LENGTH: 5
<212> TYPE: PRT
<213> ORGANISM: Homo sapiens

<400> SEQUENCE: 21

Ser Tyr Ala Ile Ser
1               5

<210> SEQ ID NO 22
<211> LENGTH: 17
<212> TYPE: PRT
<213> ORGANISM: Homo sapiens

<400> SEQUENCE: 22

Arg Ile Ile Pro Ile Leu Gly Ile Ala Asn Tyr Ala Gln Lys Phe Gln
1               5                   10                  15

Gly

<210> SEQ ID NO 23
<211> LENGTH: 12
<212> TYPE: PRT
<213> ORGANISM: Homo sapiens

<400> SEQUENCE: 23

Gly Gly Ser Tyr Gly Ser Leu Tyr Ala Phe Asp Ile
1               5                   10

<210> SEQ ID NO 24
<211> LENGTH: 13
<212> TYPE: PRT
<213> ORGANISM: Homo sapiens

<400> SEQUENCE: 24

Gly Gly Tyr Gly Gly Asn Ser Leu Tyr Ala Phe Asp Ile
1               5                   10

<210> SEQ ID NO 25
<211> LENGTH: 12
<212> TYPE: PRT
<213> ORGANISM: Homo sapiens

<400> SEQUENCE: 25

Ser Gly His Gly Tyr Ser Tyr Gly Ala Phe Asp Tyr
1               5                   10

<210> SEQ ID NO 26
<211> LENGTH: 13
<212> TYPE: PRT
<213> ORGANISM: Artificial sequence
<220> FEATURE:
<223> OTHER INFORMATION: Heavy chain CDR3 consensus
<220> FEATURE:
<221> NAME/KEY: VARIANT
<222> LOCATION: (1)..(1)
<223> OTHER INFORMATION: Xaa = absent or Gly
<220> FEATURE:
<221> NAME/KEY: VARIANT
<222> LOCATION: (2)..(2)
<223> OTHER INFORMATION: Xaa = Gly or Ser
<220> FEATURE:
```

```
<221> NAME/KEY: VARIANT
<222> LOCATION: (3)..(3)
<223> OTHER INFORMATION: Xaa = Gly or Tyr
<220> FEATURE:
<221> NAME/KEY: VARIANT
<222> LOCATION: (4)..(4)
<223> OTHER INFORMATION: Xaa = Ser, Gly or His
<220> FEATURE:
<221> NAME/KEY: VARIANT
<222> LOCATION: (5)..(5)
<223> OTHER INFORMATION: Xaa = Tyr or Gly
<220> FEATURE:
<221> NAME/KEY: VARIANT
<222> LOCATION: (6)..(6)
<223> OTHER INFORMATION: Xaa = Gly, Asn or Tyr
<220> FEATURE:
<221> NAME/KEY: VARIANT
<222> LOCATION: (8)..(8)
<223> OTHER INFORMATION: Xaa = Leu or Tyr
<220> FEATURE:
<221> NAME/KEY: VARIANT
<222> LOCATION: (9)..(9)
<223> OTHER INFORMATION: Xaa = Tyr or Gly
<220> FEATURE:
<221> NAME/KEY: VARIANT
<222> LOCATION: (13)..(13)
<223> OTHER INFORMATION: Xaa = Ile or Tyr

<400> SEQUENCE: 26

Xaa Xaa Xaa Xaa Xaa Xaa Ser Xaa Xaa Ala Phe Asp Xaa
 1               5                  10

<210> SEQ ID NO 27
<211> LENGTH: 330
<212> TYPE: DNA
<213> ORGANISM: Homo sapiens

<400> SEQUENCE: 27
cagtctgtgt tgacgcagcc tccctcagtg tctgcggccc caggacagag agtctccatc      60
tcctgctctg ggaggagctc caacattgcc agtcatgatg ttttctggta ccagcaactc     120
ccaggaacag cccccaaaat cgtcatgtat gaaactaata acgtccctg ggggattcct     180 gaccgattct ccggctccaa gtctggcacg tccgccaccc tggacatcgc cggactccag     240
actggggacg aggccgacta ttactgcgga gcatgggata cggcctgac tggtatgctg     300 ttcggcggag ggaccaaggt gaccgtccta                                     330

<210> SEQ ID NO 28
<211> LENGTH: 315
<212> TYPE: DNA
<213> ORGANISM: Homo sapiens

<400> SEQUENCE: 28
tcctatgagc tgactcagcc accctcggtg tcagtggccc caggaaagac gaccaggatt      60
acctgtgggg gagacaacat tggacgtaaa agtgtccatt ggtatcagca gaggccaggc     120
caggcccctc tcctcctcgt ctatgatgat ggcgaccggc cctcagggat ccctgaccga     180
ttctctggct ccaactctgg gaacacagcc actctgacca tcagcgggac ccaggctatg     240
gatgaggctg actattactg tcaggcgtgg gacagcaccg tggtattcgg cggagggacc     300
agactgaccg tcctg                                                     315

<210> SEQ ID NO 29
<211> LENGTH: 330
<212> TYPE: DNA
<213> ORGANISM: Homo sapiens
```

<400> SEQUENCE: 29

```
cagtctgtcg tgacgcagcc gccctcagtg tctgcggccc caggacagaa ggtcaccatc    60
tcctgctctg gaagtagctc aacattggga ataattatg tatcctggta ccagcagctc   120
ccaggaacag cccccaaact cctcatttat gacaataatg agcgactctc agggattcct   180
gaccgattct ctggttccaa gtctggcacg tcagccaccc tgggcatcag cggactccag   240
actgggacg aggccgatta ttactgcggc acatgggata gtagcctgag tgtcgtggta   300
ttcggcggag ggaccaagct gaccgtccta                                    330
```

<210> SEQ ID NO 30
<211> LENGTH: 339
<212> TYPE: DNA
<213> ORGANISM: Homo sapiens

<400> SEQUENCE: 30

```
cagtctgtgc tgacgcagcc gccctcagtg tctggggccc cagggcagag ggtcaccatc    60
tcctgcactg ggagcagctc aacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagcct ccctggccat cactgggctc   240
caggctgagg atgaggctga ttattactgc cagtcctatg acagcagcct gagtggttct   300
tatgtggtat tcggcggagg gaccaagctg accgtccta                          339
```

<210> SEQ ID NO 31
<211> LENGTH: 363
<212> TYPE: DNA
<213> ORGANISM: Homo sapiens

<400> SEQUENCE: 31

```
caggtacagc tgcagcagtc aggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240
atggagctga gcagcctgag atctgaggac acggccgtgt attactgtgc gagagggggc   300
agctatggtt ctctctatgc ttttgatatc tggggccaag ggacaatggt caccgtctca   360
agc                                                                363
```

<210> SEQ ID NO 32
<211> LENGTH: 363
<212> TYPE: DNA
<213> ORGANISM: Homo sapiens

<400> SEQUENCE: 32

```
caggtacagc tgcagcagtc aggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtat agcaaactac   180
gcacagaagt tccagggcag agtcacgatt accgcggaca atccacgag cacagcctac   240
atggagctga gcagcctgag atctgaggac acggccgtgt attactgtgc gagagggggc   300
agctatggtt ctctctatgc ttttgatatc tggggccaag ggaccagggt caccgtctca   360
agc                                                                363
```

<210> SEQ ID NO 33
<211> LENGTH: 366
<212> TYPE: DNA
<213> ORGANISM: Homo sapiens

<400> SEQUENCE: 33
caggtacagc tgcagcagtc aggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaagg atcatcccta tccttggtat agcaaactac    180
gcacagaagt tccagggcag agtcacgatt accgcggaca atccacgag cacagcctac    240 atggagctga gcagcctgag atctgaggac acggccgtgt attactgtgc gagggggggc    300
tacggtggta actccttgta tgcttttgat atctggggcc aagggacaat ggtcaccgtc    360
tcctca                                                               366

<210> SEQ ID NO 34
<211> LENGTH: 348
<212> TYPE: DNA
<213> ORGANISM: Homo sapiens

<400> SEQUENCE: 34
gaagtgcagc tggtgcagtc tggggctgag gtgaagaagc ctggggcctc agtgaaggtc     60
tcctgcaagg cttctggagg caccttcagc agctatgcta tcagctgggt gcgacaggcc    120
cctggacaag ggcttgagtg gatgggaagg atcatcccta tccttggtat agcaaactac    180
gcacagaagt tccagggcag agtcacgatt accgcggaca atccacgag cacagcctac    240 atggagctga gcagcctgag atctgaggac acggccgtgt attactgtgc gaggtcaggg    300
catggataca gctatggagc ttttgactac tggggccagg gcaccctg                 348

<210> SEQ ID NO 35
<211> LENGTH: 121
<212> TYPE: PRT
<213> ORGANISM: Homo sapiens

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly His Gly Tyr Ser Tyr Gly Ala Phe Asp Tyr Trp Gly
            100                 105                 110

Gln Gly Thr Leu Val Thr Val Ser Ser
        115                 120

<210> SEQ ID NO 36
<211> LENGTH: 363
<212> TYPE: DNA
<213> ORGANISM: Homo sapiens

```
<400> SEQUENCE: 36
caggtgcagc tggtgcaatc tggggctgag gtgaagaagc ctgggtcctc agtgaaggtc      60
tcctgcaagg cttctggagg caccttcagc agctatgcta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac      240 atggagctga gcagcctgag atctgaggac acggccgtgt attactgtgc gaggtcaggg     300
catggataca gctatggagc ttttgactac tggggccagg gcaccctggt caccgtctca     360
agc                                                                   363
```